United States Patent
Ichinose

(10) Patent No.: US 12,431,236 B2
(45) Date of Patent: Sep. 30, 2025

(54) LEARNING DEVICE, LEARNING METHOD, LEARNING PROGRAM, INFORMATION PROCESSING APPARATUS, INFORMATION PROCESSING METHOD, AND INFORMATION PROCESSING PROGRAM

(71) Applicant: FUJIFILM Corporation, Tokyo (JP)

(72) Inventor: Akimichi Ichinose, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 612 days.

(21) Appl. No.: 17/892,108

(22) Filed: Aug. 21, 2022

(65) Prior Publication Data

US 2023/0068201 A1    Mar. 2, 2023

(30) Foreign Application Priority Data

Aug. 30, 2021 (JP) ................. 2021-140166

(51) Int. Cl.
*G16H 30/40* (2018.01)
*G06T 7/00* (2017.01)
(Continued)

(52) U.S. Cl.
CPC ........... *G16H 30/40* (2018.01); *G06T 7/0012* (2013.01); *G06V 10/82* (2022.01); *G16H 50/20* (2018.01);
(Continued)

(58) Field of Classification Search
CPC ........ G16H 30/40; G16H 50/20; G16H 50/70; G06T 7/0012; G06T 2207/10072;
(Continued)

(56) References Cited

U.S. PATENT DOCUMENTS 11,062,448 B2 * 7/2021 Nakamura ............ G06T 7/0012
11,101,033 B2 * 8/2021 Tao ......................... G16H 15/00
(Continued)

FOREIGN PATENT DOCUMENTS

JP    2016197375    11/2016
JP    2019074868    5/2019
(Continued)

OTHER PUBLICATIONS

Barnard et al., "Matching Words and Pictures", Journal of Machine Learning Research 3 (2003), pp. 1107-1135 (Year: 2003).*
(Continued)

*Primary Examiner* — Jennifer Mehmood
*Assistant Examiner* — Jose M Torres
(74) *Attorney, Agent, or Firm* — JCIPRNET

(57) ABSTRACT

A processor derives a first feature amount for each of a plurality of first objects included in first data by a first neural network, derives a second feature amount for second data including one or more second objects by a second neural network, specifies a first object candidate, which is paired with the second object, from among the plurality of first objects, estimates an attribute of a pair second object, which is paired with the first object candidate, based on the first object candidate, and trains at least one of the first neural network or the second neural network such that a difference between the estimated attribute of the pair second object and an attribute of the pair second object derived from the second data is reduced.

20 Claims, 14 Drawing Sheets

(51) Int. Cl.
  *G06V 10/82* (2022.01)
  *G16H 50/20* (2018.01)
  *G16H 50/70* (2018.01)

(52) U.S. Cl.
  CPC ... *G16H 50/70* (2018.01); *G06T 2207/10072* (2013.01); *G06T 2207/20081* (2013.01); *G06T 2207/20084* (2013.01); *G06T 2207/30064* (2013.01); *G06T 2207/30096* (2013.01); *G06V 2201/031* (2022.01)

(58) Field of Classification Search
  CPC . G06T 2207/10116; G06T 2207/20081; G06T 2207/20084; G06T 2207/30064; G06T 2207/30096; G06V 10/82; G06V 2201/031
  See application file for complete search history.

(56) References Cited

U.S. PATENT DOCUMENTS

| | | | |
|---|---|---|---|
| 11,837,346 B2* | 12/2023 | Nakamura | G06F 40/30 |
| 11,978,274 B2* | 5/2024 | Ichinose | G06V 30/19007 |
| 12,039,005 B2* | 7/2024 | Hamauzu | G06V 10/255 |
| 12,183,450 B2* | 12/2024 | Ichinose | G06T 7/75 |
| 12,249,069 B2* | 3/2025 | Ichinose | G16H 30/40 |
| 12,288,611 B2* | 4/2025 | Ichinose | G06T 7/0016 |
| 12,315,633 B2* | 5/2025 | Li | G06T 7/0012 |
| 2019/0286652 A1 | 9/2019 | Habbecke et al. | |
| 2019/0295248 A1* | 9/2019 | Nakamura | G16H 30/40 |
| 2019/0371439 A1 | 12/2019 | Lisowska et al. | |
| 2020/0242762 A1 | 7/2020 | Matsuki et al. | |
| 2021/0089571 A1 | 3/2021 | Perone et al. | |
| 2021/0232860 A1 | 7/2021 | Liu et al. | |
| 2022/0076796 A1* | 3/2022 | Momoki | G06T 7/0012 |
| 2022/0358651 A1 | 11/2022 | Matsuki et al. | |
| 2022/0366151 A1* | 11/2022 | Nakamura | A61B 5/055 |
| 2022/0391599 A1* | 12/2022 | Nakamura | G06F 40/169 |
| 2022/0415459 A1* | 12/2022 | Ichinose | G16H 10/60 |
| 2022/0415461 A1* | 12/2022 | Momoki | G16H 15/00 |
| 2023/0005178 A1* | 1/2023 | Liu | G06V 30/274 |
| 2023/0005580 A1* | 1/2023 | Momoki | G16H 30/40 |
| 2023/0005601 A1* | 1/2023 | Nakamura | G16H 15/00 |
| 2023/0029934 A1* | 2/2023 | Kamon | G06T 7/0012 |
| 2023/0030794 A1 | 2/2023 | Ichinose | |
| 2023/0230241 A1* | 7/2023 | Lure | G16H 50/00 382/128 |
| 2023/0252075 A1 | 8/2023 | Habbecke et al. | |
| 2023/0360213 A1* | 11/2023 | Momoki | G16H 50/20 |
| 2023/0410305 A1* | 12/2023 | Nakamura | G16H 40/67 |
| 2023/0420096 A1* | 12/2023 | Nakamura | G06F 40/40 |
| 2024/0046028 A1* | 2/2024 | Nakamura | G06F 40/166 |
| 2024/0119750 A1* | 4/2024 | Ichinose | G16H 50/70 |
| 2024/0193932 A1* | 6/2024 | Ichinose | G06V 10/768 |
| 2024/0203101 A1* | 6/2024 | Zhang | G06V 20/70 |
| 2024/0266056 A1* | 8/2024 | Momoki | G16H 50/20 |

FOREIGN PATENT DOCUMENTS

| | | |
|---|---|---|
| JP | 2019212296 | 12/2019 |
| JP | 2021516810 | 7/2021 |
| JP | 2021117967 | 8/2021 |
| JP | 2023019734 | 2/2023 |

OTHER PUBLICATIONS

Karpathy et al., "Deep Visual-Semantic Alignments for Generaing Image Descriptions", arXiv:1412.2306v2 [cs.CV] Apr. 14, 2015, pp. 1-17 (Year: 2015).*

Lan et al., "Learning and Integrating Multi-Level Matching Features for Image-Text Retrieval", IEEE Signal Processing Letters, vol. 29, 2022, pp. 374-378 (Year: 2022).*

Pham et al., "Composing Object Relations and Attributes for Image-Text Matching", arXiv:2406.11820v1 [cs.CV] Jun. 17, 2024, pp. 1-15 (Year: 2024).*

Elad Hoffer et al., "Deep metric learning using Triplet network," arXiv: 1412.6622, Dec. 20, 2014, pp. 1-6.

Liwei Wang et al., "Learning Two-Branch Neural Networks for Image-Text Matching Tasks," arXiv: 1704.03470, Apr. 11, 2017, pp. 1-14.

"Notice of Reasons for Refusal of Japan Counterpart Application", issued on Feb. 18, 2025, with English translation thereof, p. 1-p. 11.

"Office Action of Japan Counterpart Application", issued on May 20, 2025, with English translation thereof, p. 1-p. 6.

* cited by examiner

LEARNING DEVICE, LEARNING METHOD, LEARNING PROGRAM, INFORMATION PROCESSING APPARATUS, INFORMATION PROCESSING METHOD, AND INFORMATION PROCESSING PROGRAM

CROSS REFERENCE TO RELATED APPLICATIONS

The present application claims priority under 35 U.S.C. § 119 to Japanese Patent Application No. 2021-140166 filed on Aug. 30, 2021. The above application is hereby expressly incorporated by reference, in its entirety, into the present application.

BACKGROUND

Technical Field

The present disclosure relates to a learning device, a learning method, a learning program, an information processing apparatus, an information processing method, and an information processing program.

Related Art

A method of constructing a feature space to which a feature amount, such as a feature vector, extracted from an image belongs using a trained model that has been subjected to machine learning by deep learning or the like has been proposed. For example, Deep metric learning using Triplet network, Elad Hoffer et al., 20 Dec. 2014, arXiv: 1412.6622 proposes a method of training a trained model such that the feature amounts of the images belonging to the same class get close to each other in the feature space and the feature amounts of the images belonging to different classes are separated from each other in the feature space. In addition, there is also known a technology of associating a feature amount extracted from an image with a feature amount extracted from a sentence based on a distance in a feature space (see Learning Two-Branch Neural Networks for Image-Text Matching Tasks, Liwei Wang et al., 11 Apr. 2017, arXiv: 1704.03470).

As disclosed in Learning Two-Branch Neural Networks for Image-Text Matching Tasks, Liwei Wang et al., 11 Apr. 2017, arXiv: 1704.03470, in order to accurately train the trained model that associates the image with the sentence, a large amount of teacher data in which a feature included in the image and a feature described in the sentence are associated with each other is required. However, due to the limited number of images and sentences, it may be difficult to prepare a large amount of teacher data. In particular, in the field of medical image analysis, since the number of medical images is limited, it is difficult to construct the trained model capable of associating the image with the sentence with high accuracy.

SUMMARY OF THE INVENTION

The present disclosure has been made in view of the above circumstances, and is to enable association between an image and a sentence with high accuracy.

A learning device according to the present disclosure comprises at least one processor, in which the processor derives a first feature amount for each of a plurality of first objects included in first data (for example, image data) by a first neural network, derives a second feature amount for second data (for example, text data) including one or more second objects by a second neural network, specifies a first object candidate, which is paired with the second object, from among the plurality of first objects, estimates an attribute of a pair second object, which is paired with the first object candidate, based on the first object candidate, and constructs at least one of a first derivation model that derives a feature amount for the object included in the first data or a second derivation model that derives a feature amount for the second data including the object by training at least one of the first neural network or the second neural network such that a difference between the estimated attribute of the pair second object and an attribute of the pair second object derived from the second data is reduced.

It should be noted that, in the learning device according to the present disclosure, the processor may specify the first object candidate based on a distance between the first feature amount and the second feature amount in a feature space to which the first feature amount and the second feature amount belong.

In addition, in the learning device according to the present disclosure, the processor may specify the first object candidate based on a degree of association between the first feature amount and the second feature amount.

In addition, in the learning device according to the present disclosure, the processor may estimate the attribute of the pair second object from the first feature amount for the first object candidate.

In addition, in the learning device according to the present disclosure, the processor may derive the attribute of the pair second object from the first data.

In addition, in the learning device according to the present disclosure, in a case in which a plurality of the first object candidates are specified, the processor may estimate the attribute of the pair second object from an addition value or a weighting addition value of the first feature amounts for the plurality of first object candidates.

In addition, in the learning device according to the present disclosure, in a case in which a plurality of the first object candidates are specified, the processor may estimate the attribute of the pair second object from an addition value or a weighting addition value of the plurality of first object candidates in the first data.

In addition, in the learning device according to the present disclosure, the processor may further train at least one of the first neural network or the second neural network such that, in a feature space to which the first feature amount and the second feature amount belong, a distance between the derived first feature amount and second feature amount is reduced in a case in which the first object and the second object correspond to each other, and may further train at least one of the first neural network or the second neural network such that, in the feature space, the distance between the derived first feature amount and second feature amount is increased in a case in which the first object and the second object do not correspond to each other.

In addition, in the learning device according to the present disclosure, the first data may be image data that represents an image including the first object, and the second data may be text data that represents a sentence including a description of the second object.

In addition, in the learning device according to the present disclosure, the image may be a medical image, the first object included in the image may be a lesion included in the medical image, the sentence may be an opinion sentence about the medical image, and the second object may be an opinion about the lesion in the sentence.

A first information processing apparatus according to the present disclosure comprises at least one processor, in which the processor derives a first feature amount for one or more first objects included in a target image by the first derivation model constructed by the learning device according to the present disclosure, derives a second feature amount for one or more target sentences including descriptions of a second object by the second derivation model constructed by the learning device according to the present disclosure, specifies the first feature amount corresponding to the second feature amount based on a distance between the derived first feature amount and second feature amount in a feature space, and displays the first object from which the specified first feature amount is derived, in distinction from other regions in the target image.

It should be noted that, in the first information processing apparatus according to the present disclosure, the processor may estimate an attribute of the second object, which is paired with a specified first object, based on the first object from which the specified first feature amount is derived, and may further display the estimated attribute.

In addition, in the first information processing apparatus according to the present disclosure, the processor may derive an attribute of the second object described in the target sentence, and may display the target sentence by distinguishing a description of the derived attribute different from an estimated attribute in the target sentence from other descriptions.

A second information processing apparatus according to the present disclosure comprises at least one processor, in which the processor receives input of a target sentence including a description of a second object, derives a second feature amount for the input target sentence by the second derivation model constructed by the learning device according to the present disclosure, refers to a database in which a first feature amount for one or more first objects included in a plurality of reference images, which is derived by the first derivation model constructed by the learning device according to the present disclosure, is associated with each of the reference images, to specify at least one first feature amount corresponding to the second feature amount based on a distance between the first feature amounts for the plurality of reference images and the derived second feature amount in a feature space, and specifies the reference image associated with the specified first feature amount.

A learning method according to the present disclosure comprises deriving a first feature amount for each of a plurality of first objects included in first data by a first neural network, deriving a second feature amount for second data including one or more second objects by a second neural network, specifying a first object candidate, which is paired with the second object, from among the plurality of first objects, estimating an attribute of a pair second object, which is paired with the first object candidate, based on the first object candidate, and constructing at least one of a first derivation model that derives a feature amount for the object included in the first data or a second derivation model that derives a feature amount for the second data including the object by training at least one of the first neural network or the second neural network such that a difference between the estimated attribute of the pair second object and an attribute of the pair second object derived from the second data is reduced.

A first information processing method according to the present disclosure comprises deriving a first feature amount for one or more first objects included in a target image by the first derivation model constructed by the learning device according to the present disclosure, deriving a second feature amount for one or more target sentences including descriptions of a second object by the second derivation model constructed by the learning device according to the present disclosure, specifying the first feature amount corresponding to the second feature amount based on a distance between the derived first feature amount and second feature amount in a feature space, and displaying the first object from which the specified first feature amount is derived, in distinction from other regions in the target image.

A second information processing method according to the present disclosure comprises receiving input of a target sentence including a description of a second object, deriving a second feature amount for the input target sentence by the second derivation model constructed by the learning device according to the present disclosure, referring to a database in which a first feature amount for one or more first objects included in a plurality of reference images, which is derived by the first derivation model constructed by the learning device according to the present disclosure, is associated with each of the reference images, to specify at least one first feature amount corresponding to the second feature amount based on a distance between the first feature amounts for the plurality of reference images and the derived second feature amount in a feature space, and specifying the reference image associated with the specified first feature amount.

It should be noted that the learning method, and the first and second information processing methods according to the present disclosure may be provided as a program to be executed by a computer.

According to the present disclosure, it is possible to associate the image with the sentence with a high accuracy.

DETAILED DESCRIPTION

Figure 1:
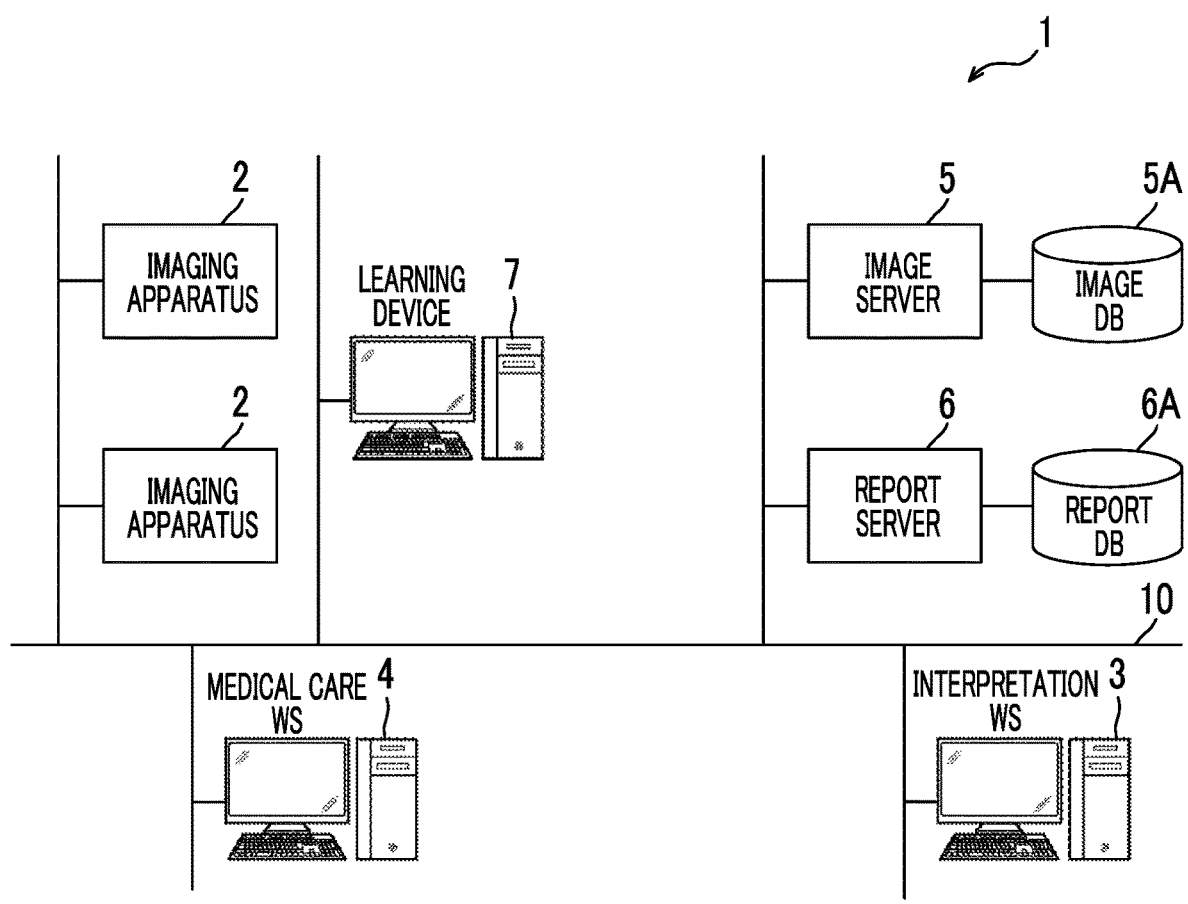
FIG. 1 is a diagram showing a schematic configuration of a medical information system to which a learning device and an information processing apparatus according to a first embodiment of the present disclosure are applied.

In the following, embodiments of the present disclosure will be described with reference to the drawings. First, a configuration of a medical information system to which a learning device and an information processing apparatus according to a first embodiment of the present disclosure are applied will be described. FIG. 1 is a diagram showing a schematic configuration of a medical information system 1. The medical information system 1 shown in FIG. 1 is a system that performs imaging of an examination target part of a patient who is a subject, the storage of a medical image acquired by imaging, the interpretation of the medical image and the creation of an interpretation report by an interpreter, and viewing of the interpretation report and the detailed observation of the medical image of an interpretation target by the doctor of the medical care department which is a request source, based on an examination order from a doctor of a medical care department by using a known ordering system.

As shown in FIG. 1, the medical information system 1 has a configuration in which a plurality of imaging apparatuses 2, a plurality of interpretation work stations (WSs) 3, a medical care WS 4, an image server 5, an image database (DB) 5A, a report server 6, a report DB 6A, and a learning device 7 are connected via a wired or wireless network 10 to be able to communicate with each other.

Each device is a computer on which an application program for functioning as a component of the medical information system 1 is installed. The application program is stored in a storage device of a server computer connected to the network 10 or a network storage in a state of being accessible from the outside, is downloaded to the computer in response to a request, and is installed. Alternatively, the imaging program is recorded on a recording medium, such as a digital versatile disc (DVD) and a compact disc read only memory (CD-ROM), is distributed, and is installed in a computer from the recording medium.

The imaging apparatus 2 is an apparatus (modality) that generates the medical image representing a diagnosis target part by imaging the diagnosis target part of the patient. Specifically, the imaging apparatus 2 is a simple X-ray imaging apparatus, a computed tomography (CT) device, a magnetic resonance imaging (MRI) device, a positron emission tomography (PET) device, and the like. The medical image generated by the imaging apparatus 2 is transmitted to the image server 5 and is then stored in the image DB 5A.

The interpretation WS 3 is a computer used by, for example, the interpreter of a radiology department to perform the interpretation of the medical image and the creation of the interpretation report, and encompasses the information processing apparatus (details will be described below) according to the present embodiment. In the interpretation WS 3, a viewing request for the medical image to the image server 5, various types of image processing for the medical image received from the image server 5, displaying of the medical image, and an input reception of an opinion sentence relating to the medical image are performed. In addition, in the interpretation WS 3, analysis processing of the medical image, support for creating the interpretation report based on the analysis result, a registration request and a viewing request for the interpretation report to the report server 6, and displaying of the interpretation report received from the report server 6 are performed. These types of processing are performed by the interpretation WS 3 executing a software program for each processing.

The medical care WS 4 is a computer used by the doctor of the medical care department to perform the detailed observation of the image, viewing of the interpretation report, the creation of an electronic medical record, and the like, and is composed of a processing apparatus, a display device, such as a display, and an input device, such as a keyboard and a mouse. In the medical care WS 4, the viewing request for the image to the image server 5, displaying of the image received from the image server 5, the viewing request for the interpretation report to the report server 6, and displaying of the interpretation report received from the report server 6 are performed. These types of processing are performed by the medical care WS 4 executing a software program for each processing.

The image server 5 is a server in which a software program providing a function of a database management system (DBMS) to a general-purpose computer is installed. In addition, the image server 5 comprises a storage constituting the image DB 5A. This storage may be a hard disk device connected to the image server 5 by a data bus, or may be a disk device connected to a network attached storage (NAS) and a storage area network (SAN) connected to the network 10. In addition, in a case in which the image server 5 receives the registration request of the medical image from the imaging apparatus 2, the image server 5 arranges the medical image in a format for a database and registers the arranged medical image in the image DB 5A.

In the image DB 5A, image data of the medical image acquired in the imaging apparatus 2 and accessory information are registered. The accessory information includes, for example, an image identification (ID) for identifying an individual medical image, a patient ID for identifying the patient, an examination ID for identifying the examination, a unique identification (UID) assigned to each medical image, an examination date and an examination time at which each medical image is generated, a type of imaging apparatus used in the examination to acquire each medical image, patient information, such as a name, an age, and a gender of the patient, an examination part (imaging part), imaging information (imaging protocol, imaging sequence, imaging method, imaging condition, use of contrast agent, and the like), and information, such as a series number or a collection number in a case in which a plurality of medical images are acquired in one examination. In addition, in the present embodiment, a first feature amount of the medical image derived as described below in the interpretation WS 3 is registered in the image DB 5A in association with the medical image.

In addition, in a case in which the viewing request from the interpretation WS 3 and the medical care WS 4 is received via the network 10, the image server 5 searches for the medical image registered in the image DB 5A and transmits the searched medical image to the interpretation WS 3 and the medical care WS 4 that are request sources.

The report server 6 incorporates the software program that provides the function of the database management system to the general-purpose computer. In a case in which the registration request for the interpretation report from the interpretation WS 3 is received, the report server 6 arranges the interpretation report in the format for a database, and registers the arranged interpretation report in the report DB 6A.

In the report DB 6A, a large number of interpretation reports including the opinion sentences created by the interpreter using the interpretation WS 3 are registered in a predetermined data format. It should be noted that the data of the interpretation report includes text data that represents the opinion sentence. The interpretation report may include, for example, information, such as the medical image of the interpretation target, the image ID for identifying the medical image, an interpreter ID for identifying the interpreter who performs the interpretation, a lesion name, positional information of the lesion, and a property of the lesion. In the present embodiment, the interpretation report and one or more medical images for which the interpretation report is created are associated with each other and registered in the report DB 6A.

In addition, in a case in which the viewing request for the interpretation report is received from the interpretation WS 3 and the medical care WS 4 via the network 10, the report server 6 searches for the interpretation report registered in the report DB 6A, and transmits the searched interpretation report to the interpretation WS 3 and the medical care WS 4, which are the request sources.

The network 10 is a wired or wireless local area network that connects various devices in a hospital. In a case in which the interpretation WS 3 is installed in another hospital or clinic, the network 10 may have a configuration in which the local area networks of respective hospitals are connected to each other via the Internet or a dedicated circuit.

Figure 2:
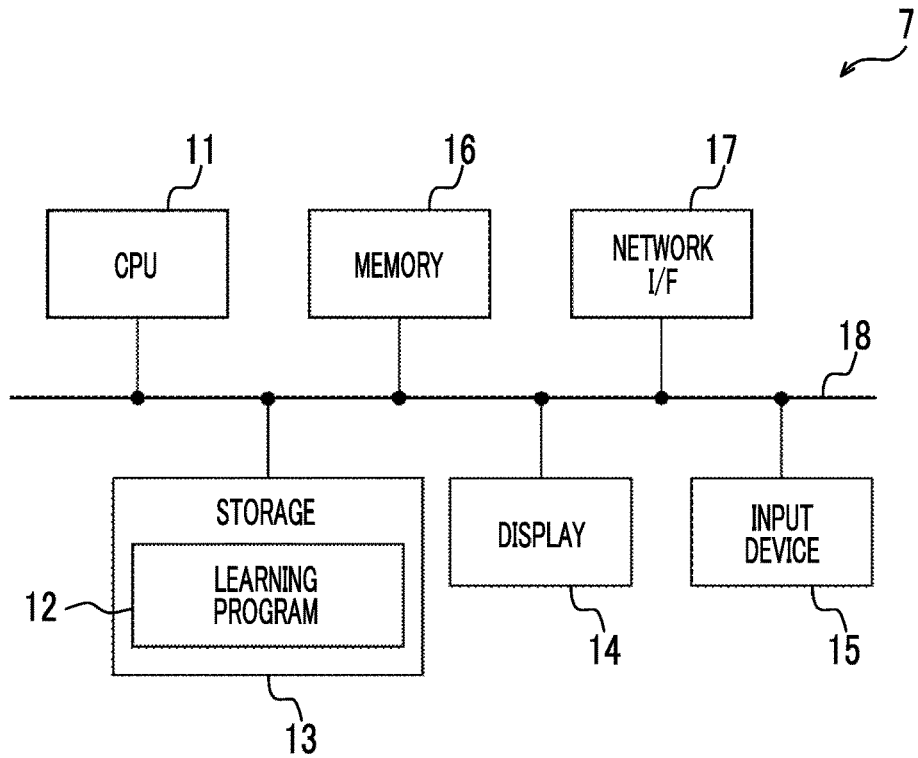
FIG. 2 is a diagram showing a schematic configuration of the learning device according to the first embodiment.

Next, the learning device 7 will be described. A hardware configuration of the learning device 7 according to the first embodiment will be described with reference to FIG. 2. As shown in FIG. 2, the learning device 7 includes a central processing unit (CPU) 11, a non-volatile storage 13, and a memory 16 as a temporary storage region. In addition, the learning device 7 includes a display 14, such as a liquid crystal display, an input device 15 consisting of a pointing device, such as the keyboard and the mouse, and a network interface (I/F) 17 connected to the network 10. The CPU 11, the storage 13, the display 14, the input device 15, the memory 16, and the network I/F 17 are connected to a bus 18. It should be noted that the CPU 11 is an example of a processor according to the present disclosure.

The storage 13 is realized by a hard disk drive (HDD), a solid state drive (SSD), and a flash memory, and the like. The storage 13 as a storage medium stores a learning program 12. The CPU 11 reads out the learning program 12 from the storage 13, develops the read-out learning program 12 in the memory 16, and executes the developed learning program 12.

Figure 3:
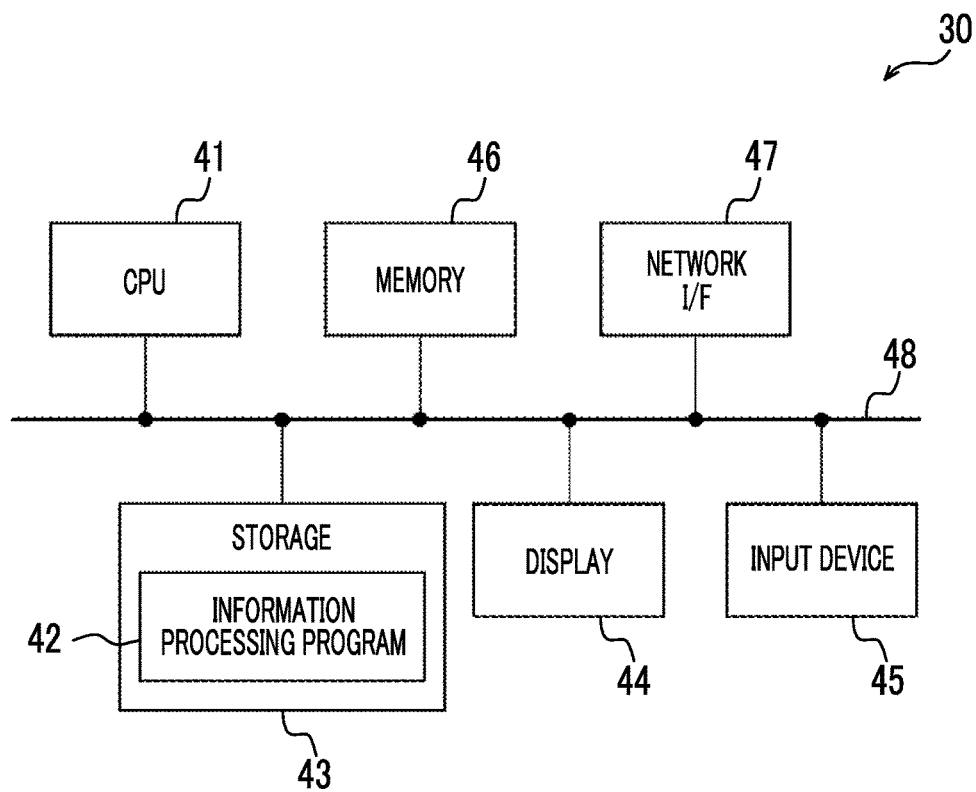
FIG. 3 is a diagram showing a schematic configuration of the information processing apparatus according to the first embodiment.

Next, an information processing apparatus 30 according to the first embodiment encompassed in the interpretation WS 3 will be described. First, a hardware configuration of the information processing apparatus 30 according to the present embodiment will be described with reference to FIG. 3. As shown in FIG. 3, the information processing apparatus 30 includes a CPU 41, a non-volatile storage 43, and a memory 46 as a temporary storage region. In addition, the information processing apparatus 30 includes a display 44, such as the liquid crystal display, an input device 45 consisting of the pointing device, such as the keyboard and the mouse, and a network I/F 47 connected to the network 10. The CPU 41, the storage 43, the display 44, the input device 45, the memory 46, and the network I/F 47 are connected to a bus 48. It should be noted that the CPU 41 is an example of the processor according to the present disclosure.

Similar to the storage 13, the storage 43 is realized by the HDD, the SSD, the flash memory, and the like. An information processing program 42 is stored in the storage 43 as the storage medium. The CPU 41 reads out the information processing program 42 from the storage 43, develops the read-out information processing program 42 in the memory 46, and executes the developed information processing program 42.

Figure 4:
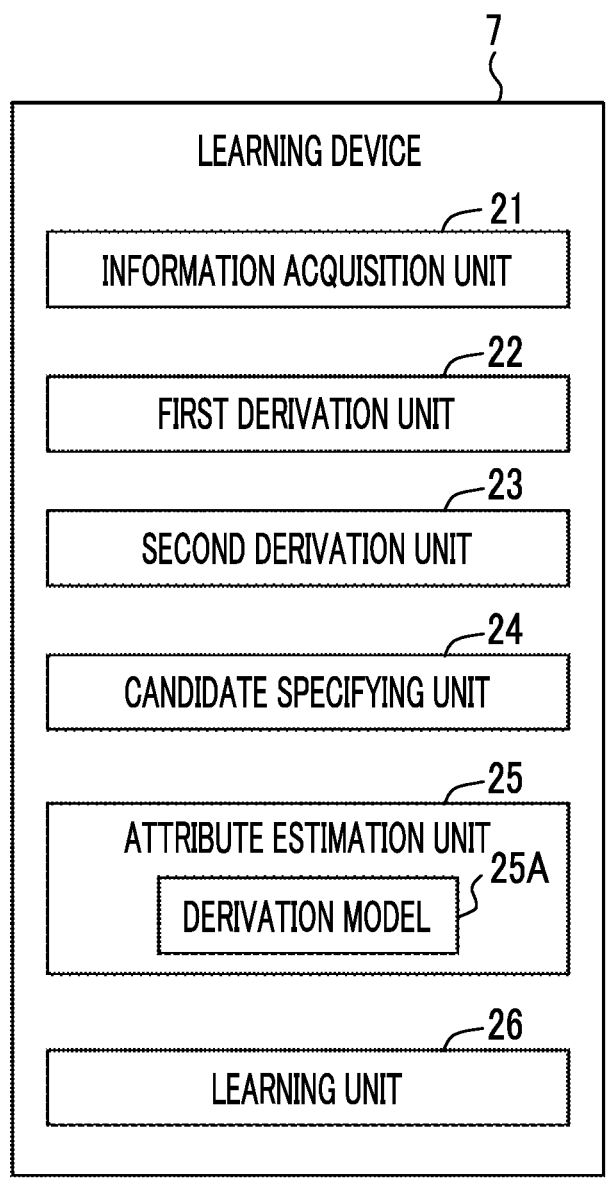
FIG. 4 is a functional configuration diagram of the learning device according to the first embodiment.

Then, a functional configuration of the learning device according to the first embodiment will be described. FIG. 4 is a diagram showing the functional configuration of the learning device according to the first embodiment. As shown in FIG. 4, the learning device 7 comprises an information acquisition unit 21, a first derivation unit 22, a second derivation unit 23, a candidate specifying unit 24, an attribute estimation unit 25, and a learning unit 26. Moreover, by the CPU 11 executing the learning program 12, the CPU 11 functions as the information acquisition unit 21, the first derivation unit 22, the second derivation unit 23, the candidate specifying unit 24, the attribute estimation unit 25, and the learning unit 26.

Figure 5:
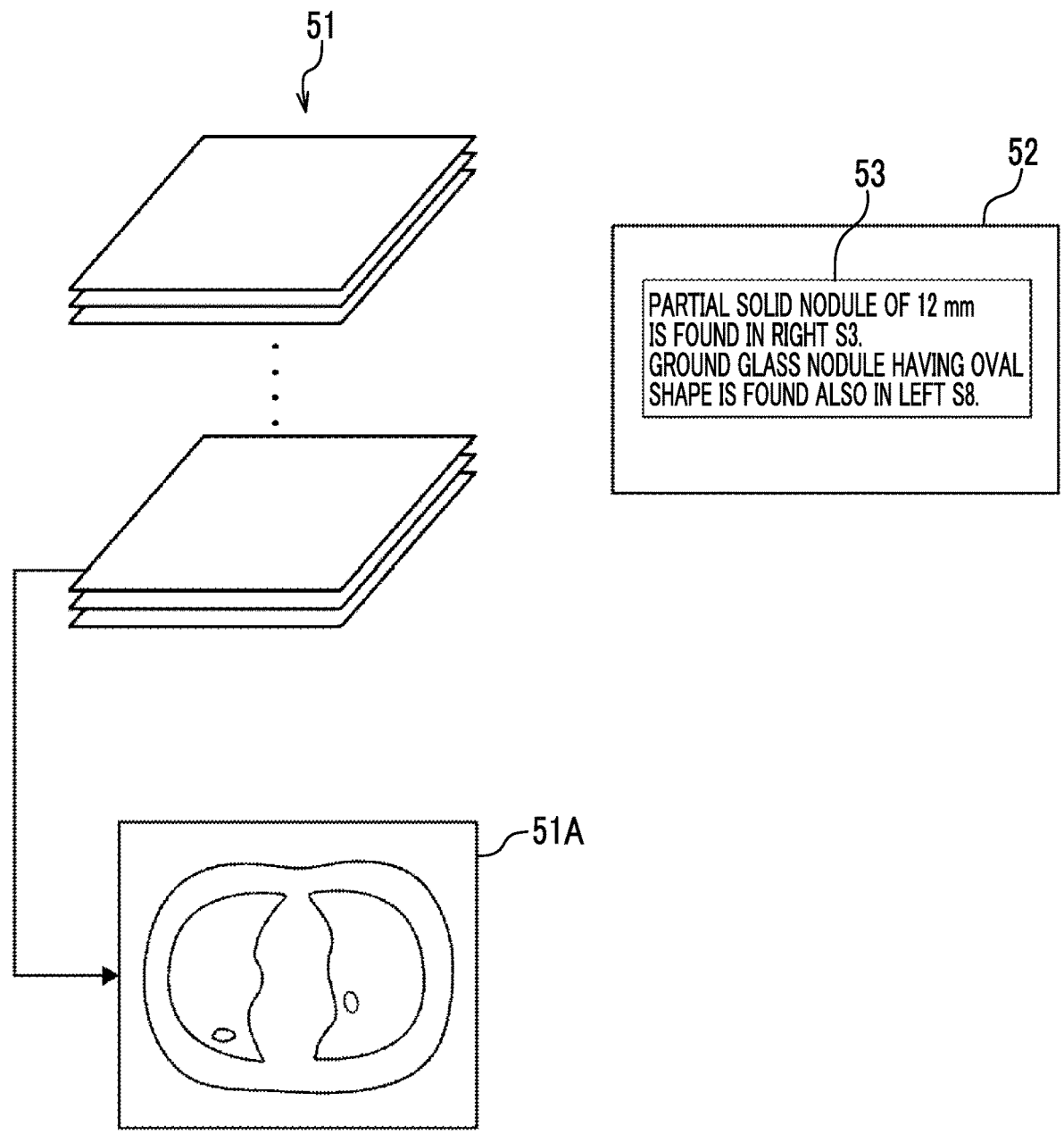
FIG. 5 is a diagram showing examples of a medical image and an interpretation report.

The information acquisition unit 21 acquires the medical image and the interpretation report from the image server 5 and the report server 6, respectively, via the network I/F 17. The medical image and the interpretation report are used to train neural networks described below. FIG. 5 is a diagram showing examples of the medical image and the interpretation report. As shown in FIG. 5, a medical image 51 is a three-dimensional image consisting of a plurality of tomographic images. In the present embodiment, the medical image 51 is a CT image of a chest of a human body. In addition, as shown in FIG. 5, the plurality of tomographic images include a tomographic image 51A including a plurality of lesions.

In addition, as shown in FIG. 5, an interpretation report 52 includes an opinion sentence 53. The description content of the opinion sentence 53 relates to the lesion included in the medical image 51, and is "A partial solid nodule of 12 mm is found in the right S3. A ground glass nodule having an oval shape is found also in the left S8." It should be noted that, although the medical image 51 and the interpretation report 52 are associated with each other, the lesion included in the medical image 51 and the individual opinion sentence included in the interpretation report 52 are not associated with each other.

Figure 6:
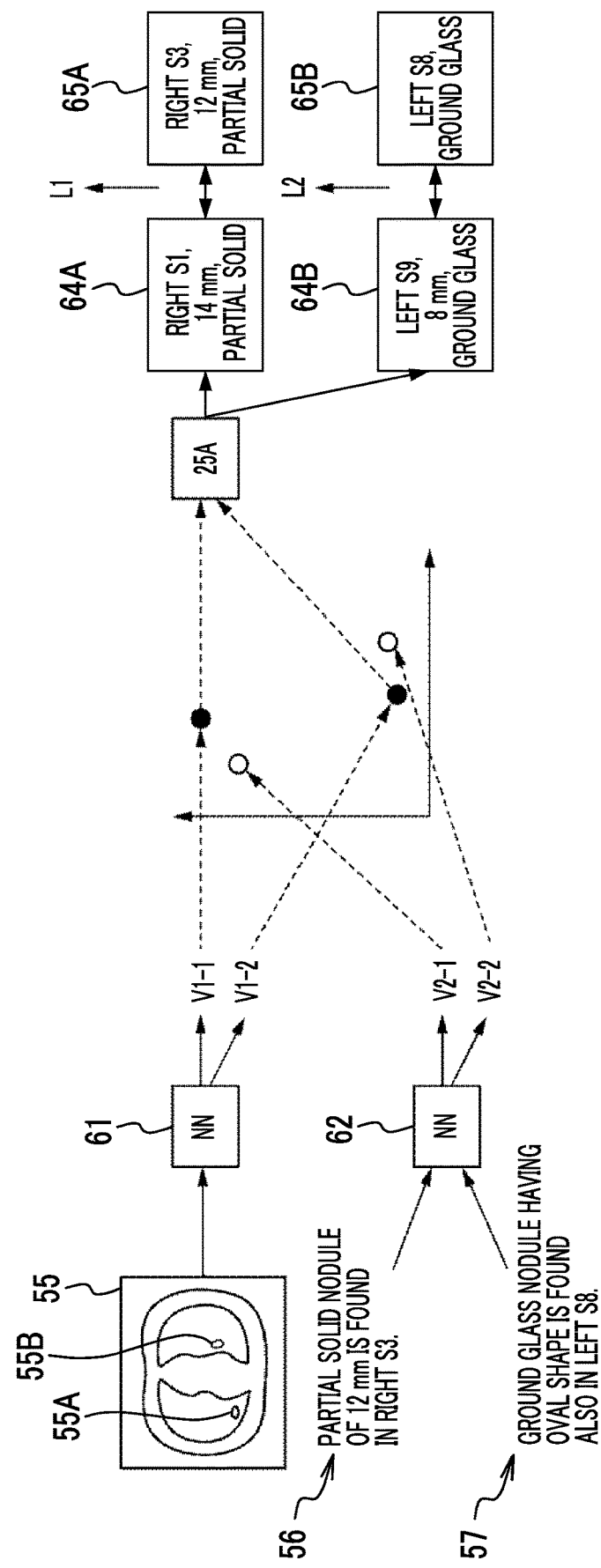
FIG. 6 is a diagram schematically showing processing performed by a first derivation unit, a second derivation unit, an attribute acquisition unit, and a learning unit in the first embodiment.

Then, the first derivation unit 22, the second derivation unit 23, the candidate specifying unit 24, the attribute estimation unit 25, and the learning unit 26 will be described. FIG. 6 is a diagram schematically showing processing performed by the first derivation unit 22, the second derivation unit 23, the candidate specifying unit 24, the attribute estimation unit 25, and the learning unit 26 in the first embodiment.

The first derivation unit 22 derives the first feature amount for a plurality of objects included in the medical image by using a first neural network (NN) 61 to construct a first derivation model that derives the feature amount for the object included in the medical image. In the present embodiment, the first neural network 61 is a convolutional neural network (CNN), but is not limited to this. As shown in FIG. 6, the first derivation unit 22 inputs an image 55, such as the medical image including the object, such as the lesion, to the first neural network 61. The image data of the image 55 is an example of the first data. The first neural network 61 extracts lesions 55A and 55B included in the image 55 as the object, and derives the feature vectors of the lesions 55A and 55B as the first feature amounts V1-1 and V1-2, respectively. It should be noted that, in the following description, the reference numerals of the first feature amounts V1-1 and V1-2 may be represented by V1.

It should be noted that the first neural network 61 may include two neural networks of a neural network that extracts the object included in the medical image and a neural network that derives the feature amount of the extracted object.

Figure 7:
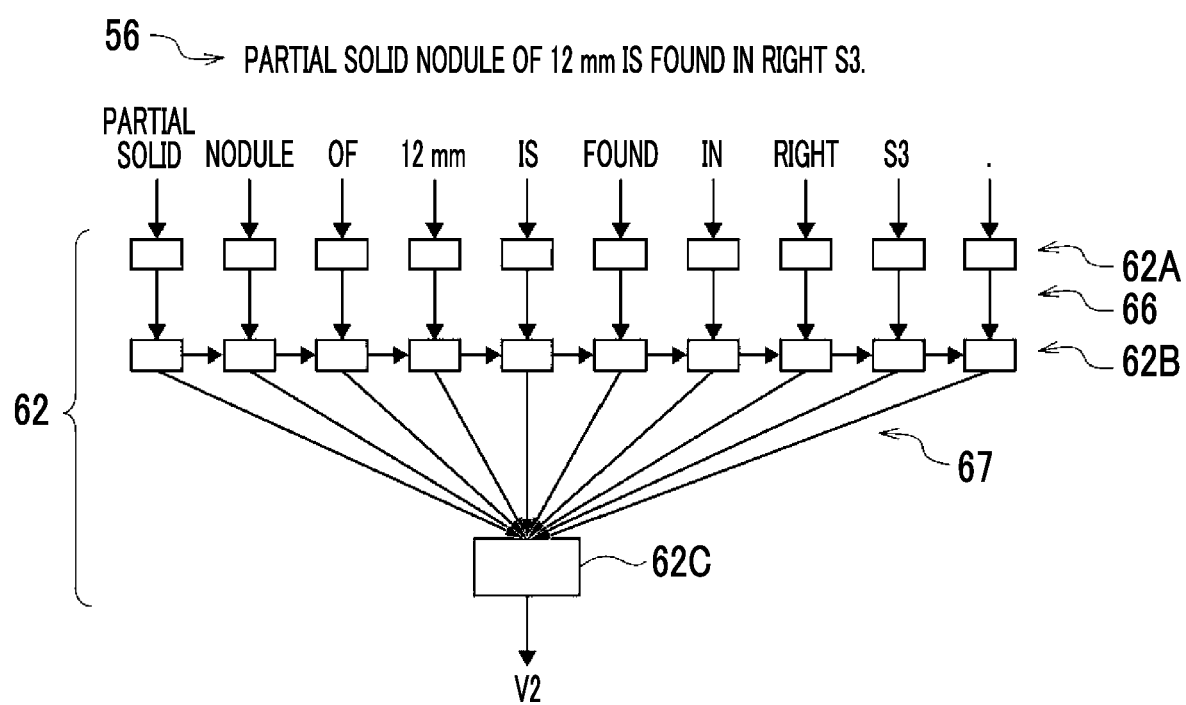
FIG. 7 is a diagram schematically showing a second neural network.

The second derivation unit 23 derives a second feature amount for a sentence including the description of the object by using a second neural network (NN) 62 to construct a second derivation model that derives the feature amount for the sentence including the description of the object. FIG. 7 is a diagram schematically showing the second neural network 62. As shown in FIG. 7, the second neural network 62 has an embedding layer 62A, a recurrent neural network layer (hereinafter, referred to as RNN layer) 62B, and a fully bonded layer 62C. The second derivation unit 23 divides the sentence into words by performing morphological analysis on the input sentence, and inputs the sentence to the embedding layer 62A. The embedding layer 62A outputs the feature vector of the word included in the input sentence. For example, in a case in which a sentence 56 describing "A partial solid nodule of 12 mm is found in the right S3." is input to the second neural network 62, the sentence 56 is divided into words of "partial solid/nodule/of/12 mm/is/found/in/right/S3/." Moreover, each of the words is input to the element of the embedding layer 62A.

The RNN layer 62B outputs a feature vector 67 considering the context of a feature vector 66 of the words. The fully bonded layer 62C integrates the feature vector 67 output by the RNN layer 62B, and outputs the feature vector of the sentence 56 input to the second neural network 62 as a second feature amount V2. It should be noted that, in a case in which the feature vector 67 output by the RNN layer 62B is input to the fully bonded layer 62C, the weighting of the feature vector 67 for important words may be increased.

Here, in the first embodiment, a second feature amount V2-1 is acquired by the sentence 56 of "A partial solid nodule of 12 mm is found in the right S3." A second feature amount V2-2 is acquired by a sentence 57 of "A ground glass nodule having an oval shape is found also in the left S8." It should be noted that, in the following description, the reference numerals of the second feature amounts V2-1 and V2-2 may be represented by V2. The text data that represents the sentences 56 and 57 is an example of the second data.

It should be noted that the second derivation unit 23 may structure the input sentence and input the unique expression obtained by the structuring to the second neural network 62 to derive the second feature amount V2. In the present embodiment, structuring means extracting the unique expression, such as the position, the opinion, and the size of the object included in the sentence, and further adding the determination result of the factuality of whether the unique expression represents the positivity, the negativity, or the suspicion to the unique expression. For example, the unique expressions of "right S3", "12 mm", and "partial solid nodule (opinion+)" can be obtained by structuring the sentence 56 of "A partial solid nodule of 12 mm is found in the right S3." Here, "opinion (+)" indicates that the factuality represents the positivity.

The candidate specifying unit 24 specifies an object candidate, which is paired with the object described in the sentence, from among the plurality of objects included in the image. In the following, the object included in the image is referred to as a first object, and the object described in the sentence is referred to as a second object. Therefore, the candidate specifying unit 24 specifies a first object candidate, which is paired with the second object, from among a plurality of first objects. It should be noted that the lesions 55A and 55B included in the image 55 are examples of the first object. In addition, at least a part of the description of the sentence 56 of "A partial solid nodule of 12 mm is found in the right S3." is an example of the second object, and at least a part of the description of the sentence 57 of "A ground glass nodule having an oval shape is found also in the left S8." is an example of the second object.

In the present embodiment, the candidate specifying unit 24 specifies the first object candidate based on the distance between the first feature amount and the second feature amount in the feature space to which the first feature amount and the second feature amount belong. Therefore, the candidate specifying unit 24 plots the first feature amount V1 and the second feature amount V2 in the feature space defined by the first feature amount V1 and the second feature amount V2. Here, since the first feature amount V1 and the second feature amount V2 are n-dimensional vectors, the feature space is also n-dimensional. It should be noted that, in FIG. 6, for the sake of description, the first feature amount V1 and the second feature amount V2 are two-dimensional, and the first feature amount V1 (V1-1 and V1-2) and the second feature amount V2 (V2-1 and V2-2) are plotted by white circles in the two-dimensional feature space.

The candidate specifying unit 24 derives the distance between each of the second feature amounts V2-1 and V2-2, and the first feature amounts V1-1 and V1-2 in the feature space. Moreover, the first object from which the first feature amount V1 of which the distance is equal to or smaller than a predetermined threshold value Th1 is derived is specified as the first object candidate. Specifically, for the second feature amount V2-1 derived from the sentence 56, the lesion 55A from which the first feature amount V1-1 is derived is specified as the first object candidate. In addition, for the second feature amount V2-2 derived from the sentence 57, the lesion 55B from which the first feature amount V1-2 is derived is specified as the first object candidate.

It should be noted that the candidate specifying unit 24 may specify the first object candidate based on a degree of association between the first feature amount V1 and the second feature amount V2. As the degree of association, a cosine similarity (inner product) between the first feature amount V1 and the second feature amount V2 can be used. In this case, the degree of association is a value of −1 to +1. The candidate specifying unit 24 specifies the first object from which the first feature amount V1 of which the degree of association is equal to or larger than a predetermined threshold value Th2 is derived as the first object candidate.

The attribute estimation unit 25 estimates an attribute of a pair second object, which is paired with the first object candidate, based on the first object candidate specified by the candidate specifying unit 24. In the present embodiment, the attribute estimation unit 25 estimates the attribute of the pair second object, which is paired with the first object candidate, from the first feature amount V1 of the first object candidate. Specifically, the attribute estimation unit 25 estimates the attribute of the pair second object, which is paired with the lesion 55A described in the sentence 56, from the first feature amount V1-1 for the lesion 55A included in the image 55, and estimates the attribute of the pair second object, which is paired with the lesion 55B described in the sentence 57, from the first feature amount V1-2 for the lesion 55B.

Therefore, the attribute estimation unit 25 includes a derivation model 25A that has been subjected to machine learning to derive the attribute from the first feature amount V1 of the first object candidate. The attribute output by the derivation model 25A is, for example, a position, a size, and a property of the lesion. It should be noted that, as the property of the object, the determination result of whether it represents the positivity or the negativity for a plurality of types of property items is derived. Examples of the property items include, a shape of the border (lobular or spicula), an absorption value (solidity or ground glass), the boundary clarity, the presence or absence of calcification, and the presence or absence of pleura invagination, for the lesion included in the lung.

The derivation model 25A consists of, for example, a convolutional neural network, and is constructed by performing machine learning such that the attribute represented by the first feature amount V1 is output in a case in which the first feature amount V1 is input. The attribute represented by the first feature amount V1 output by the attribute estimation unit 25 is the estimated attribute of the pair second object which is paired with the estimated first object candidate.

That is, since the first feature amount V1-1 represents the attribute of the lesion 55A included in the image 55, the attribute output by the derivation model 25A of the attribute estimation unit 25 by using the first feature amount V1-1 is the estimated attribute of the attribute of the second object described in the sentence 56 which is paired with the lesion 55A. In addition, since the first feature amount V1-2 represents the attribute of the lesion 55B included in the image 55, the attribute output by the derivation model 25A by using the first feature amount V1-2 is the estimated attribute of the attribute of the second object described in the sentence 57 which is paired with the lesion 55B. In the following, the estimated attribute is referred to as the estimated attribute.

In FIG. 6, "right S1", "14 mm", and "partial solid" are shown as an estimated attribute 64A based on the first feature amount V1-1. "Right S1", "14 mm", and "partial solid" are the attributes of the position, the size, and the property, respectively. In addition, "left S9", "8 mm", and "ground glass" are shown as an estimated attribute 64B based on the first feature amount V1-2. "Left S9", "8 mm", and "ground glass" are attributes of the position, the size, and the property, respectively.

It should be noted that the attribute estimation unit 25 may estimate the attribute of the second object described in the sentence which is paired with the lesions 55A and 55B from data (pixel value) of regions of the lesions 55A and 55B in the image 55, instead of the first feature amount V1. In this case, the derivation model 25A of the attribute estimation unit 25 is constructed to output the attribute from the data of the lesion region in the image.

By the way, in a case in which there are a plurality of lesions included in the image, there is a case in which there is only one sentence corresponding to the plurality of lesions. For example, in a case in which the image includes two lesions, the opinion sentence may be "Two partial solid nodules of 12 mm are found in the right S3." In this case, the first feature amount V1 is derived for each of the two lesions, but there are two candidates corresponding to one sentence in the feature space. In this case, the two first feature amounts V1 may be added and the attribute may be estimated by using the added first feature amounts V1. In this case, the two first feature amounts V1 may be weighted and added. A weighting coefficient need only be determined to be larger as the distance between the second feature amount V2 and each of the two first feature amounts V1 in the feature space is smaller.

In addition, in a case in which there are the plurality of lesions included in the image, in a case in which there is only one sentence corresponding to the plurality of lesions, the attribute of the pair second object, which is paired with the lesions 55A and 55B, may be estimated from the data (pixel value) of the regions of the lesions 55A and 55B in the image 55. In this case, the data of the regions of the lesions 55A and 55B may be added, and the attribute may be estimated by using the added data. In this case, two data may be weighted and added. The weighting coefficient need only be determined to be larger as the distance between the second feature amount and each of the two first feature amounts V1 in the feature space is smaller.

The learning unit 26 constructs the first derivation model that derives the feature amount for the object included in the image and the second derivation model that derives the feature amount for the object included in the sentence by training at least one of the first neural network 61 or the second neural network 62 such that a difference between the estimated attribute of the pair second object and the attribute of the pair second object which is paired with the first object candidate derived from the sentence.

That is, the learning unit 26 trains at least one of the first neural network 61 or the second neural network 62 such that each of a difference between the estimated attribute 64A estimated by the attribute estimation unit 25 and an attribute 65A of the pair second object derived from the sentence 56, and a difference between the estimated attribute 64B estimated by the attribute estimation unit 25 and an attribute 65B of the pair second object derived from the sentence 57 is reduced. It should be noted that, in the present embodiment, both the first neural network 61 and the second neural network 62 are trained, but the present disclosure is not limited to this. Any one of the first neural network 61 or the second neural network 62 may be only trained.

Specifically, the learning unit 26 derives the difference between the estimated attribute 64A of the sentence 56 estimated by the attribute estimation unit 25 and the attribute 65A of the sentence 56 as a loss L1. In addition, the difference between the estimated attribute 64B of the sentence 57 estimated by the attribute estimation unit 25 and the attribute 65B of the sentence 57 is derived as a loss L2. In FIG. 6, "right S3", "12 mm", and "partial solid" are shown as the attribute 65A, and "left S8" and "ground glass" are shown as the attribute 65B.

It should be noted that, in a case in which the second derivation unit 23 structures the sentences 56 and 57, the structured unique expression need only be used as the attribute of the pair second object described in the sentences 56 and 57. In addition, the attributes 65A and 65B may be derived by using a derivation model (not shown) that has been subjected to machine learning to derive the attribute of the pair second object described in the sentence from the sentence.

In addition, a dictionary in which keywords of various positions, keywords of various sizes, and keywords of various properties are registered may be prepared, and the attribute of the pair second object described in the sentence may be derived by referring to the keywords registered in the dictionary. For example, examples of the keyword of the position include "right S1, right S2, . . . ", examples of the keyword of the size include "number+mm, number+cm, large", and examples of the keyword of the property include "partial solid, ground glass, nodule, cyst, . . . ". Here, the sentence 56 is "A partial solid nodule of 12 mm is found in the right S3." Therefore, the attribute 65A of "right S3", "12 mm", and "partial solid" can be derived by referring to the dictionary.

The learning unit 26 trains the first neural network 61 and the second neural network 62 based on the derived losses L1 and L2. That is, a kernel coefficient used in the weights and convolutions of the bonding between the layers constituting each of the first neural network 61 and the second neural network 62 is trained such that the losses L1 and L2 are reduced.

Specifically, the learning unit 26 repeatedly performs learning until the losses L1 and L2 are equal to or smaller than a predetermined threshold value. It should be noted that the learning unit 26 may repeatedly perform learning a predetermined number of times. As a result, the first derivation model and the second derivation model that derive the first feature amount V1 and the second feature amount V2 are constructed such that the distance in the feature space is reduced in a case in which the object included in the image and the object described in the sentence correspond to each other, and the distance in the feature space is increased in a case in which the object included in the image and the object described in the sentence do not correspond to each other.

The first derivation model and the second derivation model constructed in this way are transmitted to the interpretation WS 3 and used in the information processing apparatus according to the first embodiment.

Figure 8:
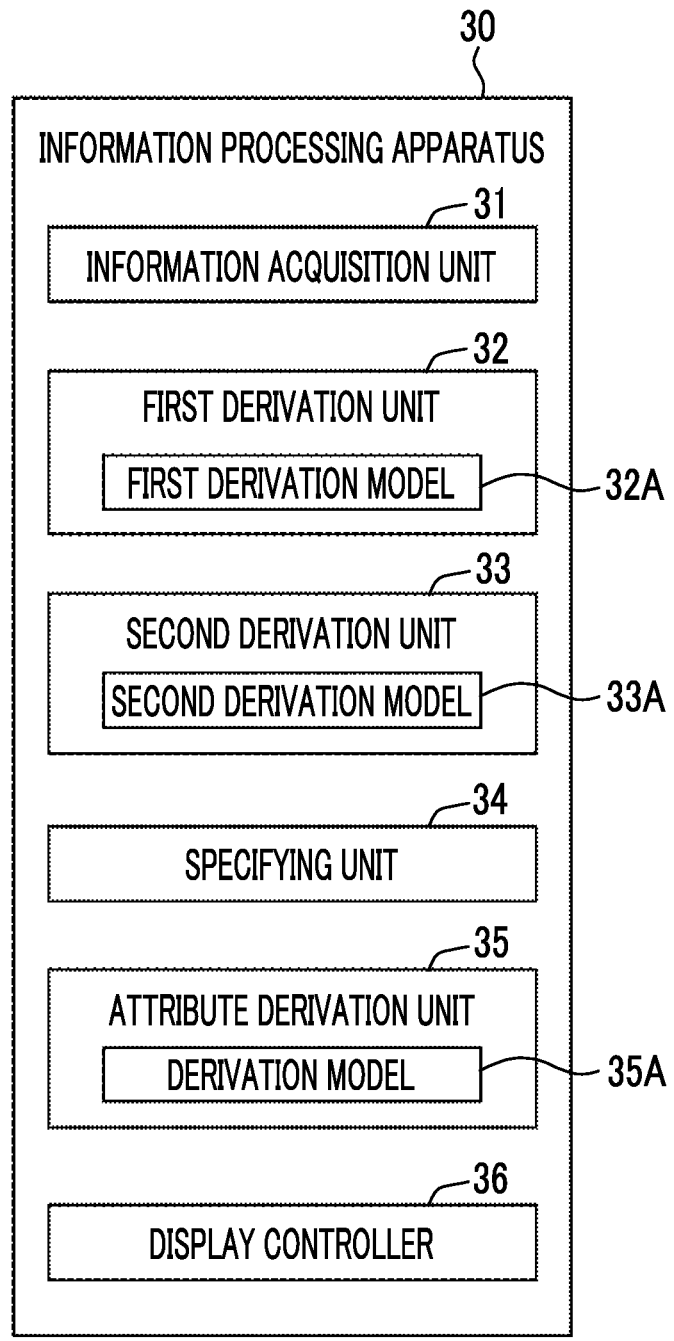
FIG. 8 is a functional configuration diagram of the information processing apparatus according to the first embodiment.

Then, a functional configuration of the information processing apparatus according to the first embodiment will be described. FIG. 8 is a diagram showing the functional configuration of the information processing apparatus according to the first embodiment. As shown in FIG. 8, the information processing apparatus 30 comprises an information acquisition unit 31, a first analysis unit 32, a second analysis unit 33, a specifying unit 34, an attribute derivation unit 35, and a display controller 36. Moreover, by the CPU 41 executing the information processing program 42, the CPU 41 functions as the information acquisition unit 31, the first analysis unit 32, the second analysis unit 33, the specifying unit 34, the attribute derivation unit 35, and the display controller 36.

The information acquisition unit 31 acquires a target medical image G0, which is the interpretation target, from the image server 5 in response to an instruction from the input device 45 by the interpreter who is an operator.

The first analysis unit 32 analyzes the target medical image G0 using a first derivation model 32A constructed by the learning device 7 described above to derive the first feature amount V1 for the object, such as the lesion, included in the target medical image G0. In the present embodiment, the target medical image G0 includes two objects, and the first feature amounts V1-1 and V1-2 are derived for each of the two objects.

Here, in the information processing apparatus 30 according to the first embodiment, the interpretation report is generated by the interpreter interpreting the target medical image G0 in the interpretation WS 3 and inputting the opinion sentence including an interpretation result by using the input device 45. The second analysis unit 33 derives the second feature amount V2 for the input opinion sentence by analyzing the input opinion sentence using the second derivation model 33A constructed by the learning device 7 described above.

Figure 9:
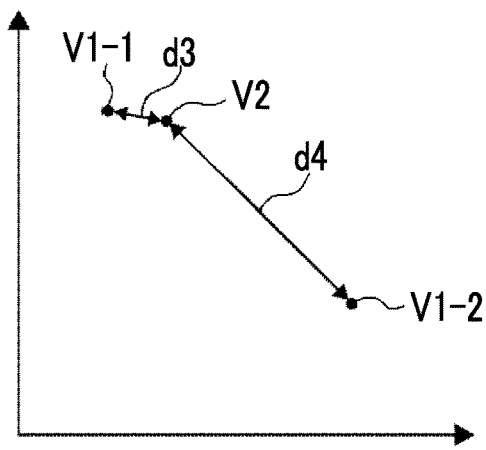
FIG. 9 is a diagram for describing specifying of a first feature amount.

The specifying unit 34 derives the distance between the first feature amount V1 derived by the first analysis unit 32 and the second feature amount V2 derived by the second analysis unit 33 in the feature space. Moreover, the first feature amount V1 corresponding to the second feature amount V2 is specified based on the derived distance. FIG. 9 is a diagram for describing specifying of the first feature amount. It should be noted that, in FIG. 9, the feature space is shown in two dimensions for the sake of description. As shown in FIG. 9, in a case in which a distance d3 between the first feature amount V1-1 and the second feature amount V2 is compared with a distance d4 between the first feature amount V1-2 and the second feature amount V2 in the feature space, d3<d4. Therefore, the specifying unit 34 specifies the first feature amount corresponding to the second feature amount V2 as the first feature amount V1-1.

The attribute derivation unit 35 derives the attribute of the object from which the first feature amount V1-1 is derived based on the specified first feature amount V1-1. Therefore, the attribute derivation unit 35 includes a derivation model 35A similar to the derivation model 25A of the attribute estimation unit 25 of the learning device 7. The attribute derivation unit 35 derives the attribute of the object from which the first feature amount V1-1 is derived by the derivation model 35A. For example, the derivation model 35A derives "position: right lung lower lobe S6, size: 23 mm, property: partial solid" as the attribute of the lesion 73 included in the target medical image G0.

Figure 10:
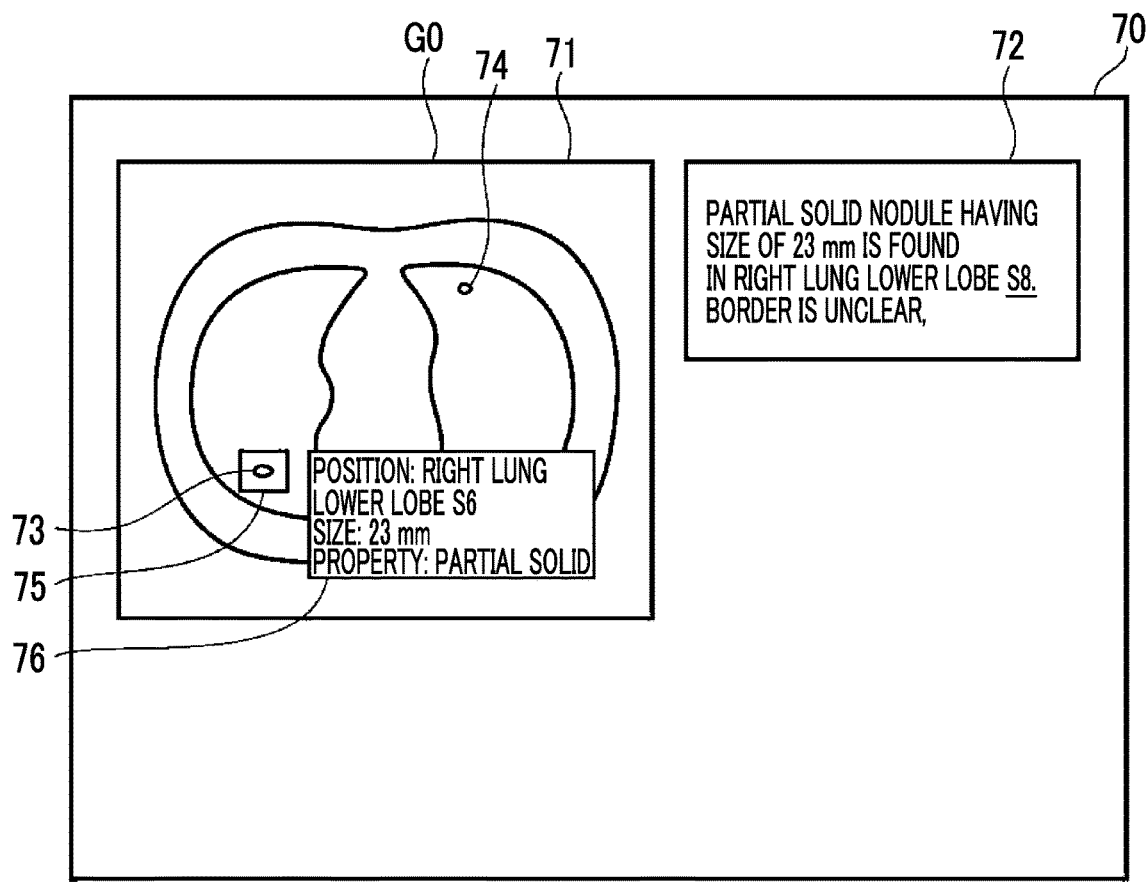
FIG. 10 is a diagram showing a creation screen of the interpretation report.

The display controller 36 displays the object from which the specified first feature amount is derived, in distinction from other regions in the target medical image G0. FIG. 10 is a diagram showing a creation screen of the interpretation report displayed on the interpretation WS 3. As shown in FIG. 10, a creation screen 70 of the interpretation report includes an image display region 71 and a sentence display region 72. The target medical image G0 is displayed in the image display region 71. In FIG. 10, the target medical image G0 is one tomographic image constituting the three-dimensional image of the chest. The opinion sentence input by the interpreter is displayed in the sentence display region 72. In FIG. 10, the opinion sentence of "A partial solid nodule having a size of 23 mm is found in the right lung lower lobe S8. A border is unclear," is displayed. The second opinion sentence is in the middle of the description.

The target medical image G0 shown in FIG. 10 includes a lesion 73 in the right lung and a lesion 74 in the left lung. In a case in which the first feature amount V1-1 derived for the lesion 73 of the right lung is compared with the first feature amount V1-2 derived for the lesion 74 of the left lung, the distance from the second feature amount V2 derived for the opinion sentence of "A partial solid nodule having a size of 23 mm is found in the right lung lower lobe S8" is smaller in the first feature amount V1-1. Therefore, the display controller 36 displays the lesion 73 of the right lung in distinction from other regions in the target medical image G0. In FIG. 10, by surrounding the lesion 73 of the right lung by a rectangular mark 75, the lesion 73 is displayed in distinction from other regions, but the present disclosure is not limited to this. A mark of any shape, such as an arrow, can be used.

In addition, on the right side of the lesion 73 in the target medical image G0, an annotation 76 in which the attribute is described is displayed. The annotation 76 includes the description of "position: right lung lower lobe S6, size: 23 mm, property: partial solid". Here, positional information included in the opinion sentence displayed in the sentence display region 72 is "right lung lower lobe S8", whereas positional information included in the attribute derived from the first feature amount V1-1 is "right lung lower lobe S6". Therefore, in the opinion sentence displayed in the sentence display region 72, the display controller 36 underlines in a portion of "S8" which is a difference from the attribute included in the annotation 76. It should be noted that, as long as the difference can be emphasized, a text color or a thickness of the text may be changed without being limited to underline.

Figure 11:
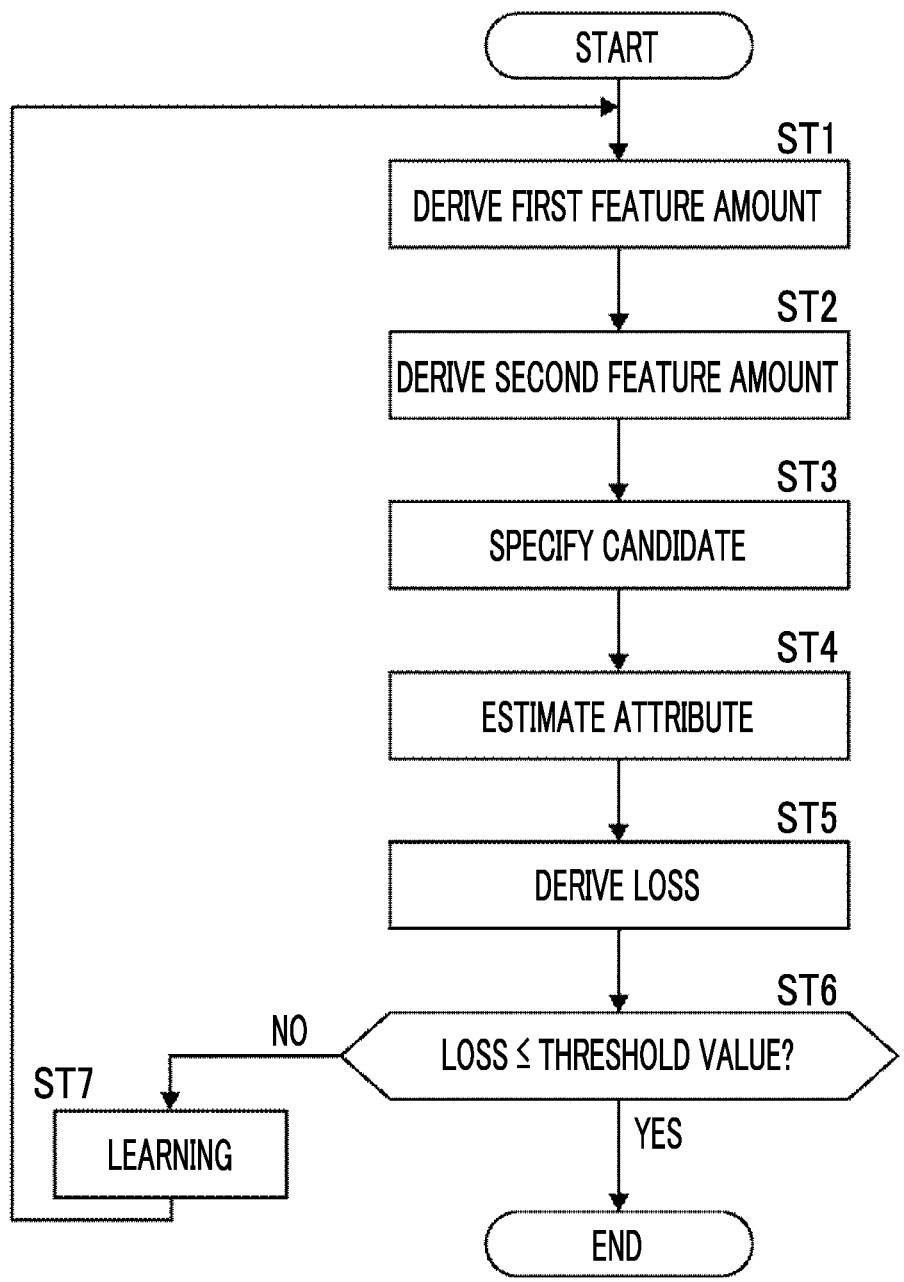
FIG. 11 is a flowchart showing learning processing performed in the first embodiment.

Then, processing performed in the first embodiment will be described. FIG. 11 is a flowchart of learning processing according to the first embodiment. It should be noted that, the image and the interpretation report used in learning are acquired from the image server 5 and the report server 6 by the information acquisition unit 21, respectively, and stored in the storage 13. In addition, a learning end condition is that the loss is equal to or smaller than the predetermined threshold value.

First, the first derivation unit 22 derives the first feature amount V1 for the object included in the image by the first neural network 61 (step ST1). In addition, the second derivation unit 23 derives the second feature amount V2 for the sentence including the description of the object by the second neural network 62 (step ST2). It should be noted that the processing of step ST2 may be performed first, or the processing of step ST1 and step ST2 may be performed in parallel.

Next, the candidate specifying unit 24 specifies the object candidate, which is paired with the second object described in the sentence, from among the plurality of first objects included in the image (candidate specification: step ST3). Moreover, the attribute estimation unit 25 estimates the attribute of the pair second object, which is paired with the first object candidate, based on the first object candidate specified by the candidate specifying unit 24 (step ST4).

Next, the learning unit 26 derives the loss, which is the difference between the estimated attribute of the pair second object and the attribute of the pair second object derived from the sentence (step ST5). Moreover, it is determined whether or not the loss is equal to or smaller than the predetermined threshold value (step ST6). In a case in which a negative determination is made in step ST6, at least one of the first neural network 61 or the second neural network 62 is trained such that the loss is reduced (step ST7), the processing returns to step ST1, and the processing of steps ST1 to ST6 is repeatedly performed. In a case in which a positive determination is made in step ST6, the processing ends.

Figure 12:
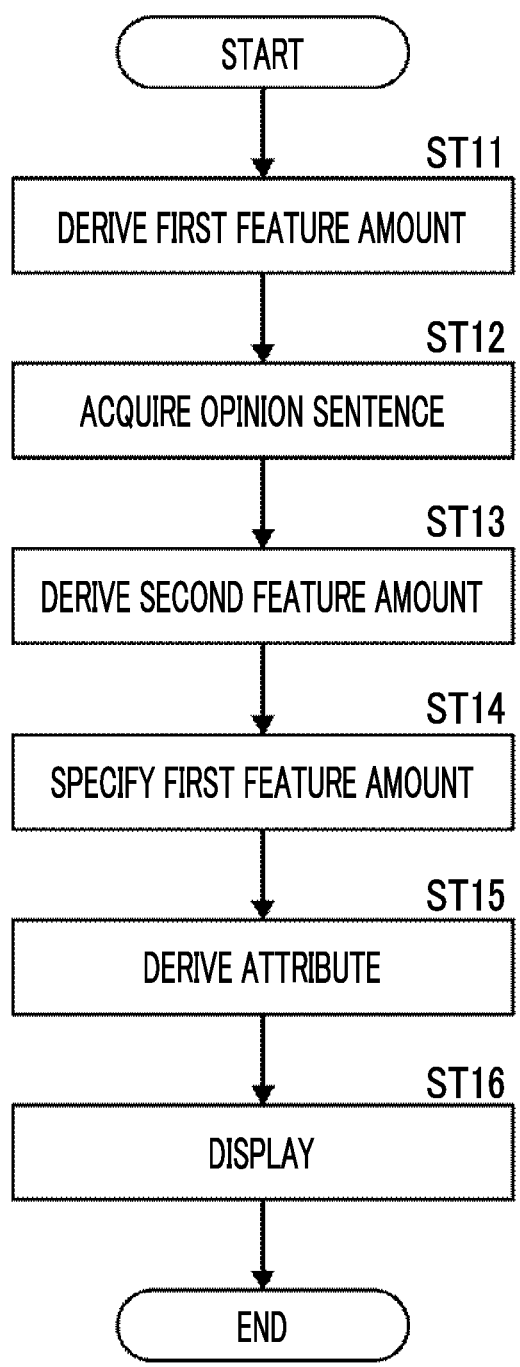
FIG. 12 is a flowchart showing information processing performed in the first embodiment.

Then, information processing according to the first embodiment will be described. FIG. 12 is a flowchart of the information processing according to the first embodiment. It should be noted that, the target medical image G0, which is a processing target, is acquired by the information acquisition unit 31 and stored in the storage 43. First, the first analysis unit 32 analyzes the target medical image G0 using the first derivation model 32A to derive the first feature amount V1 for the object, such as the lesion, included in the target medical image G0 (step ST11).

Then, the information acquisition unit 31 acquires the opinion sentence input by the interpreter using the input device 45 (step ST12), and the second analysis unit 33 analyzes the input opinion sentence using the second derivation model 33A to derive the second feature amount V2 for the input opinion sentence (step ST13).

Subsequently, the specifying unit 34 derives the distance between the first feature amount V1 derived by the first analysis unit 32 and the second feature amount V2 derived by the second analysis unit 33 in the feature space, and specifies the first feature amount V1 corresponding to the second feature amount V2 based on the derived distance (step ST14). Further, the attribute derivation unit 35 derives the attribute of the object from which the first feature amount V1 is derived (step ST15). Moreover, the display controller 36 displays the object from which the specified first feature amount V1 is derived, in distinction from other regions in the target medical image G0, and displays the annotation 76 in which the attribute is described (step ST16), and the processing ends.

As described above, in the learning device according to the first embodiment, the first object candidate, which is paired with the second object described in the sentence, is specified from among the plurality of first objects included in the image, the attribute of the pair second object, which is paired with the first object candidate, is estimated based on the first object candidate, and the first derivation model 32A and the second derivation model 33A are constructed by training at least one of the first neural network 61 or the second neural network 62 such that the difference between the estimated attribute of the pair second object and the attribute of the pair second object derived from the sentence.

Therefore, by applying the first derivation model 32A and the second derivation model 33A constructed by learning to the information processing apparatus 30 according to the first embodiment, even in a case in which the object included in the image and the object described in the sentence do not have a one-to-one association with each other, the first feature amount V1 and the second feature amount V2 are derived such that the image including the object and the sentence including the description of the object included in the image are associated with each other. Therefore, by using the derived first feature amount V1 and second feature amount V2 it is possible to accurately associate the image with the sentence.

In addition, since it is possible to accurately associate the image with the sentence, it is possible to accurately specify the object described in the input opinion sentence in the medical image in a case of creating the interpretation report for the medical image.

It should be noted that the information processing apparatus according to the first embodiment comprises the attribute derivation unit 35, but the present disclosure is not limited to this. The information processing apparatus does not have to comprise the attribute derivation unit 35. In this case, the annotation in which the attribute is described is not displayed.

It should be noted that, in the first embodiment, although the first neural network 61 and the second neural network 62 are trained such that the difference between the estimated attribute of the pair second object and the attribute of the pair second object derived from the sentence is reduced, in addition to this, the combination of the medical image and the interpretation report corresponding to the medical image may be used as teacher data to train the first and second neural networks 61 and 62. In the following, this case will be described as a second embodiment of the learning device.

Figure 13:
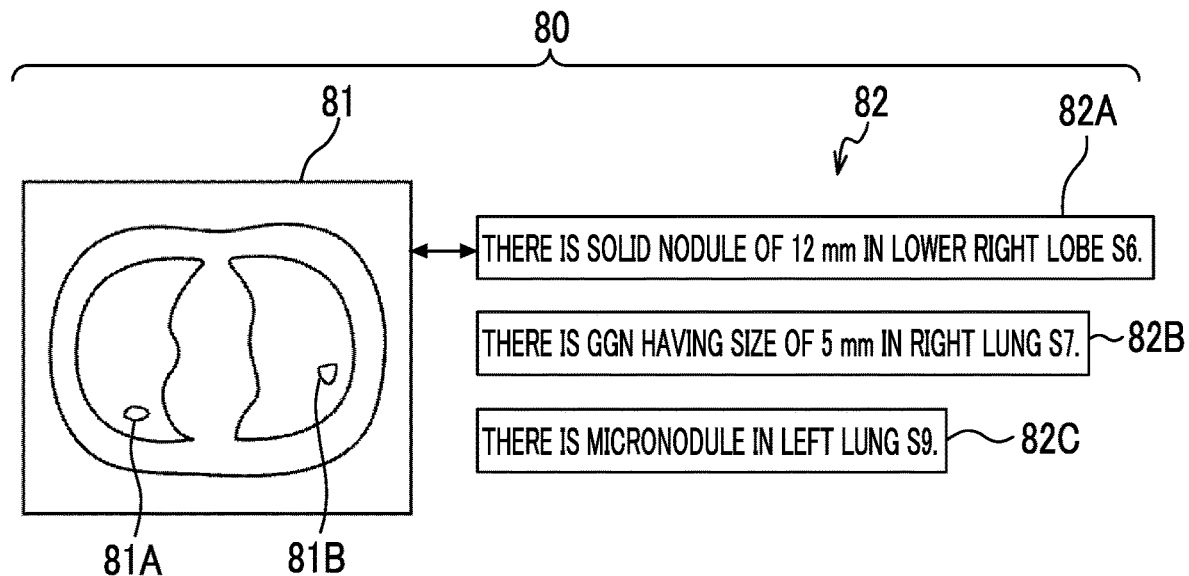
FIG. 13 is a diagram showing teacher data used in a learning device according to a second embodiment.

In the learning device according to the second embodiment, the combination of the medical image and the interpretation report corresponding to the medical image is used as the teacher data to train the first and second neural networks 61 and 62. FIG. 13 is a diagram showing the teacher data used in the second embodiment. As shown in FIG. 13, teacher data 80 consists of a teacher image 81 and an interpretation report 82 corresponding to the teacher image 81. The teacher image 81 is a tomographic image of the lung, and includes, as the first object, the lesions 81A and 81B in the lower right lobe S6 and the lower left lobe S8, respectively.

The interpretation report 82 includes three opinion sentences 82A to 82C. The opinion sentence 82A is "There is a solid nodule of 12 mm in the lower right lobe S6." The opinion sentence 82B is "There is a ground glass nodule (GGN) having a size of 5 mm in the right lung S7." The opinion sentence 82C is "There is a micronodule in the left lung S9." Here, since the teacher image 81 includes the lesion 81A in the lower right lobe S6, the opinion sentence 82A among the three opinion sentences 82A to 82C corresponds to the lesion 81A. It should be noted that the teacher image 81 is one tomographic image of the plurality of tomographic images constituting the three-dimensional image. The opinion sentences 82B and 82C are generated as a result of interpreting the tomographic images other than the teacher image 81. Therefore, the teacher image 81 and the opinion sentences 82B and 82C do not correspond to each other. In addition, the teacher image 81 includes the lesion 81B in the lower left lobe S8, but does not correspond to all of the three opinion sentences 82A to 82C.

In the second embodiment, the first derivation unit 22 derives the feature amounts of the lesions 81A and 81B of the teacher image 81 as first feature amounts V1-3 and V1-4 by the first neural network 61. In addition, the second derivation unit 23 derives the feature amounts of the opinion sentences 82A to 82C as second feature amounts V2-3, V2-4, and V2-5 by the second neural network 62.

Moreover, in the second embodiment, the candidate specifying unit 24 specifies the first object candidate, which is paired with the second object described in the corresponding opinion sentence 82A, from among the plurality of first objects (lesions 81A and 81B) included in the teacher image 81. That is, the candidate specifying unit 24 specifies the lesion 81A as the first object candidate.

In addition, the attribute estimation unit 25 estimates the attribute of the pair second object, which is paired with the lesion 81A described in the opinion sentence 82A, based on the lesion 81A which is the first object candidate specified by the candidate specifying unit 24.

The learning unit 26 trains the first neural network 61 and the second neural network 62 such that the difference between the estimated attribute of the pair second object and the attribute of the pair second object derived from the opinion sentence 82A is reduced.

Figure 14:
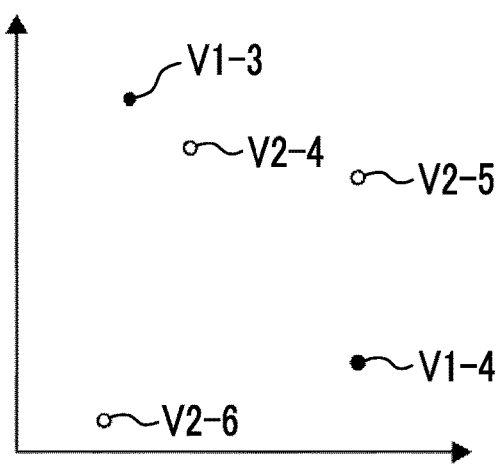
FIG. 14 is a diagram for describing a plot of a feature amount in the second embodiment.

Further, in the second embodiment, the learning unit 26 plots the first feature amounts V1-3 and V1-4 and the second feature amounts V2-3, V2-4, and V2-5 in the feature space. FIG. 14 is a diagram for describing the plot of the feature amount in the second embodiment. It should be noted that, also in FIG. 14, the feature space is shown in two dimensions for the sake of description.

Moreover, in the second embodiment, the learning unit 26 trains the first and second neural networks 61 and 62 based on the correspondence relationship between the lesions 81A and 81B included in the teacher image 81 in the teacher data 80 and the opinion sentence. That is, the learning unit 26 further trains the first and second neural networks 61 and 62 such that, in the feature space, the first feature amount V1-3 and the second feature amount V2-4 get close to each other, and the first feature amount V1-3 and the second feature amounts V2-5 and V2-6 are separated from each other. In this case, in the learning unit 26, the first and second neural networks 61 and 62 may be trained such that a degree of separation between the first feature amount V1-3 and the second feature amount V2-5 is smaller than a degree of separation between the first feature amount V1-3 and the second feature amount V2-6. In addition, the learning unit 26 trains the first and second neural networks 61 and 62 such that the first feature amount V1-4, and the second feature amounts V2-4, V2-5, and V2-6 are separated from each other in the feature space. It should be noted that any of learning based on the difference in the attributes or learning based on the correspondence relationship between the object included in the teacher image in the teacher data and the opinion sentence may be performed first.

As described above, in the learning device according to the second embodiment, learning based on the correspondence relationship between the object included in the teacher image in the teacher data and the opinion sentence is further performed. Therefore, the first and second neural networks 61 and 62 can be trained with higher accuracy, and as a result, it is possible to construct the first derivation model 32A and the second derivation model 33A that can derive the feature amounts with higher accuracy.

Figure 15:
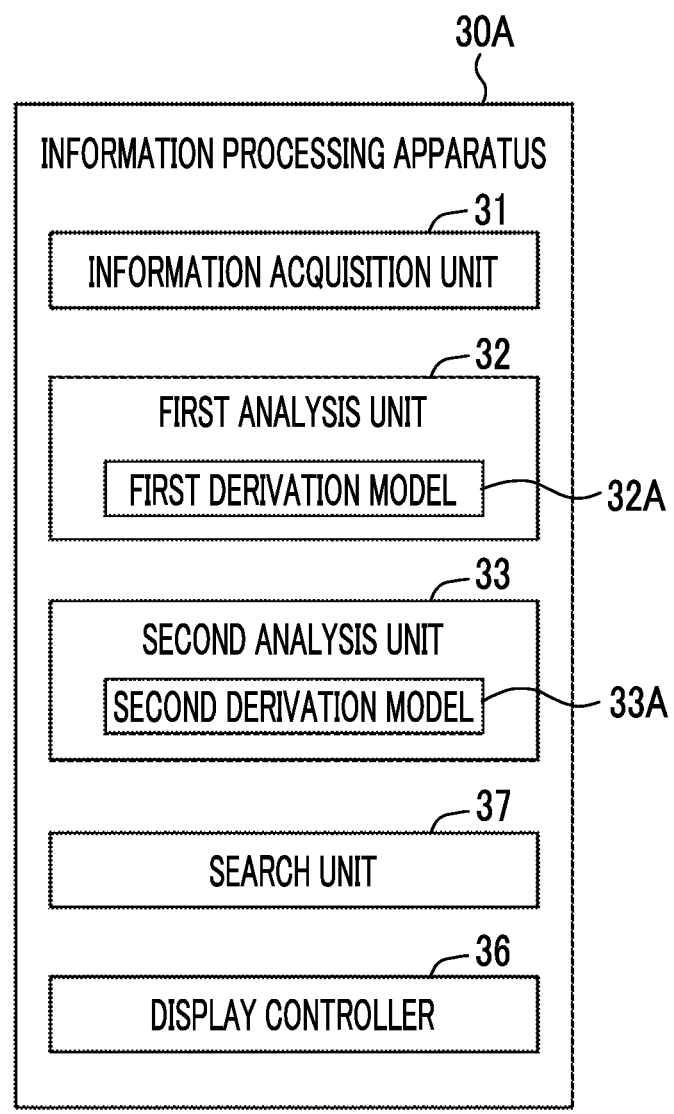
FIG. 15 is a functional configuration diagram of an information processing apparatus according to the second embodiment.

Then, the second embodiment of the information processing apparatus will be described. FIG. 15 is a functional configuration diagram of the information processing apparatus according to the second embodiment. It should be noted that, in FIG. 15, the same configurations as those in FIG. 8 are denoted by the same reference numerals, and the detailed description thereof will be omitted. As shown in FIG. 15, an information processing apparatus 30A according to the second embodiment is different from the information processing apparatus according to the first embodiment in that the attribute derivation unit 35 is not provided, and a search unit 37 is provided instead of the specifying unit 34.

In the information processing apparatus 30A according to the second embodiment, the information acquisition unit 31 acquires a large number of medical images stored in the image server 5. Moreover, the first analysis unit 32 derives the first feature amount V1 for each of the medical images. The information acquisition unit 31 transmits the first feature amount V1 to the image server 5. In the image server 5, the medical image is stored in the image DB 5A in association with the first feature amount V1. The medical image registered in the image DB 5A in association with the first feature amount V1 is referred to as a reference image in the following description.

In addition, in the information processing apparatus 30A according to the second embodiment, the interpretation report is generated by the interpreter interpreting the target medical image G0 in the interpretation WS 3 and inputting the opinion sentence including the interpretation result by using the input device 45. The second analysis unit 33 derives the second feature amount V2 for the input opinion sentence by analyzing the input opinion sentence using the second derivation model 33A constructed by the learning device 7 described above.

Figure 16:
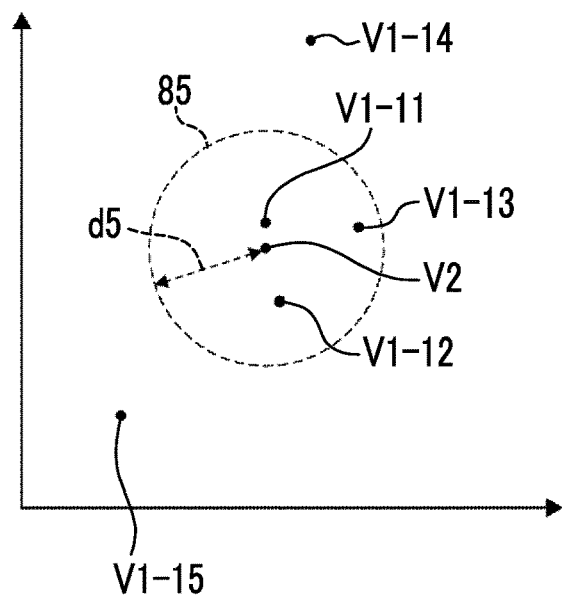
FIG. 16 is a diagram for describing a search.

The search unit 37 refers to the image DB 5A to search for the reference image associated with the first feature amount V1 having a small distance from the second feature amount V2 derived by the second analysis unit 33 in the feature space. FIG. 16 is a diagram for describing the search performed in the information processing apparatus 30A according to the second embodiment. It should be noted that, also in FIG. 16, the feature space is shown in two dimensions for the sake of description. In addition, for the sake of description, five first feature amounts V1-11 to V1-15 are plotted in the feature space.

The search unit 37 specifies the first feature amount having the distance from the second feature amount V2 within a predetermined threshold value in the feature space.

In FIG. 16, a circle 85 having a radius d5 centered on the second feature amount V2 is shown. The search unit 37 specifies the first feature amount included in the circle 85 in the feature space. In FIG. 16, three first feature amounts V1-11 to V1-13 are specified.

The search unit 37 searches the image DB 5A for the reference image associated with the specified first feature amounts V1-11 to V1-13, and acquires the searched reference image from the image server 5.

Figure 17:
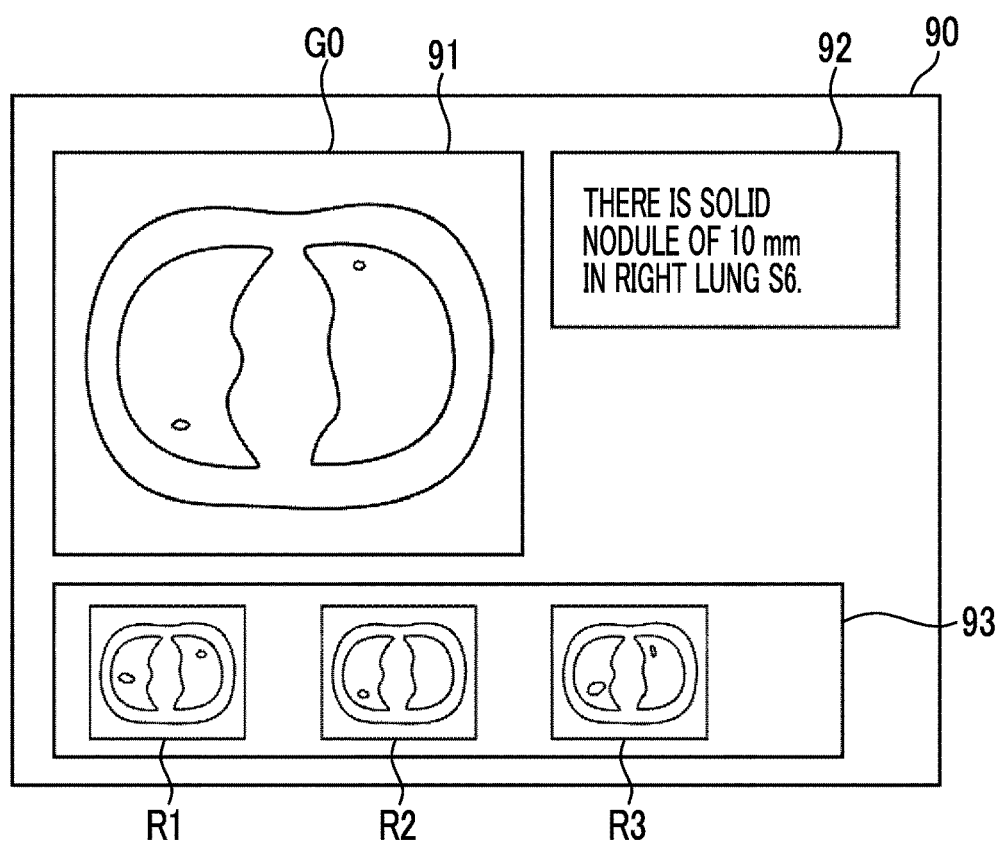
FIG. 17 is a diagram showing a display screen.

The display controller 36 displays the acquired reference image on the display 44. FIG. 17 is a diagram showing a display screen in the information processing apparatus 30A according to the second embodiment. As shown in FIG. 17, a display screen 90 includes an image display region 91, a sentence display region 92, and a result display region 93. The target medical image G0 is displayed in the image display region 91. In FIG. 17, the target medical image G0 is one tomographic image constituting the three-dimensional image of the chest. The opinion sentence input by the interpreter is displayed in the sentence display region 92. In FIG. 17, the opinion sentence of "There is the solid nodule of 10 mm in the right lung S6." is displayed.

The reference image searched by the search unit 37 is displayed in the result display region 93. In FIG. 17, three reference images R1 to R3 are displayed in the result display region 93.

Figure 18:
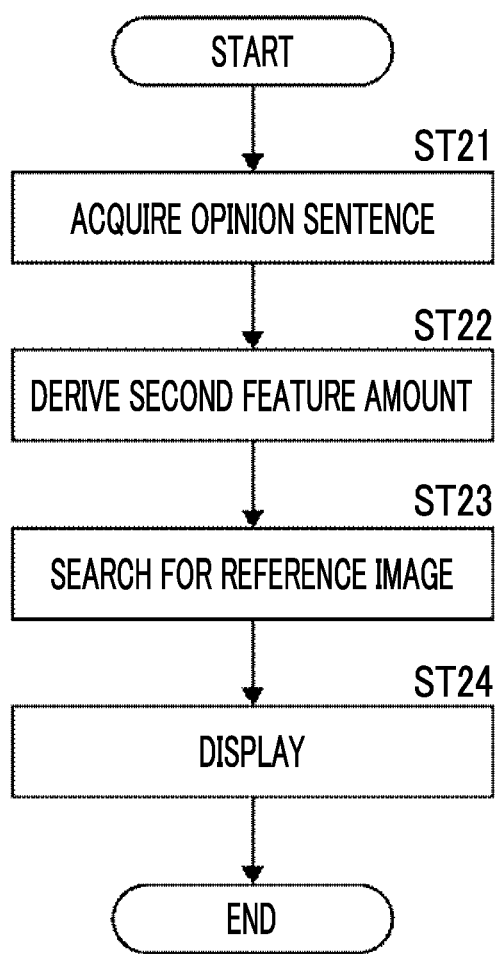
FIG. 18 is a flowchart showing information processing performed in the second embodiment.

Then, information processing according to the second embodiment will be described. FIG. 18 is a flowchart of the information processing according to the second embodiment. It should be noted that, the first feature amount of the reference image is derived by the first analysis unit 32, and the first feature amounts are registered in the image DB 5A in association with the reference image. In addition, the target medical image G0 is displayed on the display 44 by the display controller 36. In the second embodiment, the information acquisition unit 31 acquires the opinion sentence input by the interpreter using the input device 45 (step ST21), and the second analysis unit 33 analyzes the input opinion sentence using the second derivation model 33A to derive the second feature amount V2 for the object described the input opinion sentence (step ST22).

Subsequently, the search unit 37 refers to the image DB 5A and searches for the reference image associated with the first feature amount V1 having a small distance from the second feature amount V2 (step ST23). Moreover, the display controller 36 displays the searched reference image on the display 44 (step ST24), and the processing ends.

The reference images R1 to R3 searched in the second embodiment are the medical images having similar features to the opinion sentences input by the interpreter. Since the opinion sentences relate to the target medical image G0, the reference images R1 to R3 have similar cases to the target medical image G0. Therefore, according to the second embodiment, it is possible to interpret the target medical image G0 with reference to the reference image having a similar case. In addition, the interpretation report for the reference image can be acquired from the report server 6 and used to create the interpretation report for the target medical image G0.

It should be noted that, in each of the embodiments described above, at least one of the first neural network 61 or the second neural network 62 is trained such that the difference between the estimated attribute of the pair second object and the attribute of the pair second object derived from the sentence is reduced, but the derivation model 25A of the attribute estimation unit 25 may further be trained such that the difference is reduced.

In addition, in each of the embodiments described above, the derivation model that derives the feature amounts of the medical image and the opinion sentence of the medical image is constructed, but the present disclosure is not limited to this. For example, it is needless to say that the technology of the present disclosure can be applied to a case of constructing a derivation model that derives feature amounts of a photographic image and a sentence, such as a comment, corresponding to the photographic image.

In addition, in each of the embodiments described above, the image and the sentence are used as the first data and the second data according to the present disclosure, but the present disclosure is not limited to this. As the first data and the second data according to the present disclosure, data, such as a motion picture and a sound, may be used.

In addition, in each of the embodiments described above, for example, as the hardware structure of the processing unit that executes various types of processing, such as the information acquisition unit 21, the first derivation unit 22, the second derivation unit 23, the candidate specifying unit 24, the attribute estimation unit 25, and the learning unit 26 of the learning device 7, and the information acquisition unit 31, the first analysis unit 32, the second analysis unit 33, the specifying unit 34, the attribute derivation unit 35, the display controller 36, and the search unit 37 of the information processing apparatuses 30 and 30A, the following various processors can be used. As described above, the various processors include, in addition to the CPU which is a general-purpose processor that executes the software (program) to function as the various processing units described above, a programmable logic device (PLD), which is a processor of which a circuit configuration can be changed after manufacturing, such as a field programmable gate array (FPGA), a dedicated electric circuit, which is a processor having a circuit configuration specially designed to execute specific processing, such as an application specific integrated circuit (ASIC), and the like.

One processing unit may be composed of one of the various processors, or may be composed of a combination of two or more processors of the same type or different types (for example, a combination of a plurality of FPGAs or a combination of a CPU and an FPGA). In addition, a plurality of processing units may be composed of one processor. A first example of a configuration in which the plurality of processing units are composed of one processor includes a form in which one processor is composed of a combination of one or more CPUs and software and the processor functions as the plurality of processing units, as represented by the computer, such as a client and a server. A second example thereof includes a form in which a processor that realizes the function of the entire system including the plurality of processing units by one integrated circuit (IC) chip is used, as represented by a system on chip (SoC) or the like. In this way, the various processing units are composed of one or more of the various processors as the hardware structure.

Further, as the hardware structure of the various processors, more specifically, an electric circuit (circuitry) in which circuit elements, such as semiconductor elements, are combined can be used.

What is claimed is:
1. A learning device comprising:
   at least one processor,
   wherein the processor
      derives a first feature amount for each of a plurality of first objects included in first data by a first neural network, derives a second feature amount for second data including one or more second objects by a second neural network, specifies a first object candidate, which is paired with the second object, from among the plurality of first objects, estimates an attribute of a pair second object, which is paired with the first object candidate, based on the first object candidate, and constructs at least one of a first derivation model that derives a feature amount for the object included in the first data or a second derivation model that derives a feature amount for the second data including the object by training at least one of the first neural network or the second neural network such that a difference between the estimated attribute of the pair second object and an attribute of the pair second object derived from the second data is reduced.

2. The learning device according to claim 1, wherein the processor specifies the first object candidate based on a distance between the first feature amount and the second feature amount in a feature space to which the first feature amount and the second feature amount belong.

3. The learning device according to claim 1, wherein the processor specifies the first object candidate based on a degree of association between the first feature amount and the second feature amount.

4. The learning device according to claim 1, wherein the processor estimates the attribute of the pair second object from the first feature amount for the first object candidate.

5. The learning device according to claim 1, wherein the processor derives the attribute of the pair second object from the first data.

6. The learning device according to claim 4, wherein, in a case in which a plurality of the first object candidates are specified, the processor estimates the attribute of the pair second object from an addition value or a weighting addition value of the first feature amounts for the plurality of first object candidates.

7. The learning device according to claim 5, wherein, in a case in which a plurality of the first object candidates are specified, the processor estimates the attribute of the pair second object from an addition value or a weighting addition value of the plurality of first object candidates in the first data.

8. The learning device according to claim 1, wherein the processor further trains at least one of the first neural network or the second neural network such that, in a feature space to which the first feature amount and the second feature amount belong, a distance between the derived first feature amount and second feature amount is reduced in a case in which the first object and the second object correspond to each other, and further trains at least one of the first neural network or the second neural network such that, in the feature space, the distance between the derived first feature amount and second feature amount is increased in a case in which the first object and the second object do not correspond to each other.

9. The learning device according to claim 1, wherein the first data is image data that represents an image including the first object, and the second data is text data that represents a sentence including a description of the second object.

10. The learning device according to claim 9, wherein the image is a medical image, the first object included in the image is a lesion included in the medical image, the sentence is an opinion sentence about the medical image, and the second object is an opinion about the lesion in the sentence.

11. An information processing apparatus comprising:
at least one processor,
wherein the processor derives a first feature amount for one or more first objects included in a target image by the first derivation model constructed by the learning device according to claim 9, derives a second feature amount for one or more target sentences including descriptions of a second object by the second derivation model constructed by the learning device according to claim 9, specifies the first feature amount, which is derived by using the first derivation model, corresponding to the second feature amount, which is derived by using the second derivation model, based on a distance between the derived first feature amount and second feature amount in a feature space, and displays the first object from which the specified first feature amount is derived, in distinction from other regions in the target image.

12. The information processing apparatus according to claim 11,
wherein the processor estimates an attribute of the second object described in the one or more target sentences, which is paired with a specified first object, based on the first object from which the specified first feature amount is derived, and further displays the estimated attribute of the second object described in the one or more target sentences and paired with the specified first object.

13. The information processing apparatus according to claim 11,
wherein the processor derives an attribute of the second object described in the target sentence, and displays the target sentence by distinguishing a description of the derived attribute different from an estimated attribute in the target sentence from other descriptions.

14. An information processing apparatus comprising:
at least one processor,
wherein the processor receives input of a target sentence including a description of a second object, derives a second feature amount for the input target sentence by the second derivation model constructed by the learning device according to claim 9, refers to a database in which a first feature amount for one or more first objects included in a plurality of reference images, which is derived by the first derivation model constructed by the learning device according to claim 9, is associated with each of the reference images, to specify at least one first feature amount corresponding to the derived second feature amount for the input target sentence based on a distance between the first feature amounts for the plurality of reference images and the derived second feature amount in a feature space, and specifies the reference image associated with the specified first feature amount.

15. A learning method comprising:

deriving a first feature amount for each of a plurality of first objects included in first data by a first neural network;

deriving a second feature amount for second data including one or more second objects by a second neural network;

specifying a first object candidate, which is paired with the second object, from among the plurality of first objects;

estimating an attribute of a pair second object, which is paired with the first object candidate, based on the first object candidate; and constructing at least one of a first derivation model that derives a feature amount for the object included in the first data or a second derivation model that derives a feature amount for the second data including the object by training at least one of the first neural network or the second neural network such that a difference between the estimated attribute of the pair second object and an attribute of the pair second object derived from the second data is reduced.

16. An information processing method comprising:

deriving a first feature amount for one or more first objects included in a target image by the first derivation model constructed by the learning device according to claim 9;

deriving a second feature amount for one or more target sentences including descriptions of a second object by the second derivation model constructed by the learning device according to claim 9;

specifying the first feature amount, which is derived by using the first derivation model, corresponding to the second feature amount, which is derived by using the second derivation model, based on a distance between the derived first feature amount and second feature amount in a feature space; and displaying the first object from which the specified first feature amount is derived, in distinction from other regions in the target image.

17. An information processing method comprising:

receiving input of a target sentence including a description of a second object;

deriving a second feature amount for the input target sentence by the second derivation model constructed by the learning device according to claim 9;

referring to a database in which a first feature amount for one or more first objects included in a plurality of reference images, which is derived by the first derivation model constructed by the learning device according to claim 9, is associated with each of the reference images, to specify at least one first feature amount corresponding to the derived second feature amount for the input target sentence based on a distance between the first feature amounts for the plurality of reference images and the derived second feature amount in a feature space; and specifying the reference image associated with the specified first feature amount.

18. A non-transitory computer-readable storage medium that stores a learning program causing a computer to execute:

a procedure of deriving a first feature amount for each of a plurality of first objects included in first data by a first neural network;

a procedure of deriving a second feature amount for second data including one or more second objects by a second neural network;

a procedure of specifying a first object candidate, which is paired with the second object, from among the plurality of first objects;

a procedure of estimating an attribute of a pair second object, which is paired with the first object candidate, based on the first object candidate; and a procedure of constructing at least one of a first derivation model that derives a feature amount for the object included in the first data or a second derivation model that derives a feature amount for the second data including the object by training at least one of the first neural network or the second neural network such that a difference between the estimated attribute of the pair second object and an attribute of the pair second object derived from the second data is reduced.

19. A non-transitory computer-readable storage medium that stores an information processing program causing a computer to execute:

a procedure of deriving a first feature amount for one or more first objects included in a target image by the first derivation model constructed by the learning device according to claim 9;

a procedure of deriving a second feature amount for one or more target sentences including descriptions of a second object by the second derivation model constructed by the learning device according to claim 9;

a procedure of specifying the first feature amount, which is derived by using the first derivation model, corresponding to the second feature amount, which is derived by using the second derivation model, based on a distance between the derived first feature amount and second feature amount in a feature space; and a procedure of displaying the first object from which the specified first feature amount is derived, in distinction from other regions in the target image.

20. A non-transitory computer-readable storage medium that stores an information processing program causing a computer to execute:

a procedure of receiving input of a target sentence including a description of a second object;

a procedure of deriving a second feature amount for the input target sentence by the second derivation model constructed by the learning device according to claim 9;

a procedure of referring to a database in which a first feature amount for one or more first objects included in a plurality of reference images, which is derived by the first derivation model constructed by the learning device according to claim 9, is associated with each of the reference images, to specify at least one first feature amount corresponding to the derived second feature amount for the input target sentence based on a distance between the first feature amounts for the plurality of reference images and the derived second feature amount in a feature space; and a procedure of specifying the reference image associated with the specified first feature amount.

* * * * *